United States Patent
Lingoes et al.

(10) Patent No.: US 10,813,857 B2
(45) Date of Patent: Oct. 27, 2020

(54) HETEROGENOUS COSMETIC INK COMPOSITION FOR INKJET PRINTING APPLICATIONS

(71) Applicant: The Procter & Gamble Company, Cincinnati, OH (US)

(72) Inventors: Janette Villalobos Lingoes, Cincinnati, OH (US); Thomas Elliot Rabe, Baltimore, MD (US); Jeremy Chang, Dayton, OH (US); Ajay Suthar, Lexington, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/262,968

(22) Filed: Jan. 31, 2019

(65) Prior Publication Data
US 2019/0231661 A1    Aug. 1, 2019

Related U.S. Application Data

(60) Provisional application No. 62/624,920, filed on Feb. 1, 2018.

(51) Int. Cl.
*A61K 8/29*     (2006.01)
*A61Q 1/02*    (2006.01)
(Continued)

(52) U.S. Cl.
CPC .............. *A61K 8/29* (2013.01); *A61K 8/19* (2013.01); *A61K 8/8147* (2013.01);
(Continued)

(58) Field of Classification Search
CPC .......... A61K 8/29; A61K 8/19; A61K 8/8152; A61K 8/8147; A61K 2800/805;
(Continued)

(56) References Cited

U.S. PATENT DOCUMENTS

| 4,782,109 A | 11/1988 | Dulaney |
| 6,341,831 B1 | 1/2002 | Weber |

(Continued)

FOREIGN PATENT DOCUMENTS

| EP | 1010420 A1 | 6/2000 |
| EP | 1236776 A1 | 9/2002 |

(Continued)

OTHER PUBLICATIONS

Case 15117 Search report; PCT/US2019/016222; dated Apr. 25, 2019; 16 Pages.

(Continued)

*Primary Examiner* — Carlos A Azpuru
(74) *Attorney, Agent, or Firm* — Melissa G. Krasovec

(57) ABSTRACT

A cosmetic ink composition comprises a particulate material, a polymeric dispersant having a weight average molecular weight of less than about 20,000 daltons, and a polymeric rheology modifier. The particulate material can have a Particle Size Distribution D50 of about 100 nm to about 2,000 nm. The cosmetic ink composition can undergo controlled syneresis, forming a weak colloidal gel phase and a particle-lean, low viscosity phase, which can be printed without interventions such as agitation, mixing, or re-circulation to homogenize the composition.

11 Claims, 3 Drawing Sheets

(51) Int. Cl.
*A61K 8/81* (2006.01)
*C09D 11/107* (2014.01)
*A61K 8/19* (2006.01)
*C09D 11/322* (2014.01)

(52) U.S. Cl.
CPC ............ *A61K 8/8152* (2013.01); *A61Q 1/02* (2013.01); *C09D 11/107* (2013.01); *C09D 11/322* (2013.01); *A61K 2800/10* (2013.01); *A61K 2800/26* (2013.01); *A61K 2800/41* (2013.01); *A61K 2800/43* (2013.01); *A61K 2800/48* (2013.01); *A61K 2800/546* (2013.01); *A61K 2800/548* (2013.01); *A61K 2800/594* (2013.01); *A61K 2800/805* (2013.01); *A61K 2800/87* (2013.01)

(58) Field of Classification Search
CPC ............ A61K 2800/10; A61K 2800/87; A61K 2800/594; A61K 2800/48; A61K 2800/26; A61K 2800/546; A61K 2800/43; A61K 2800/41; C09D 11/322; C09D 11/107; A61Q 1/02
See application file for complete search history.

(56) References Cited

U.S. PATENT DOCUMENTS

| | | | |
|---|---|---|---|
| 6,543,893 | B2 | 4/2003 | Desormeaux |
| 8,007,062 | B2 | 8/2011 | Edgar |
| 8,466,213 | B2 | 6/2013 | Ueno |
| 8,695,610 | B2 | 4/2014 | Samain |
| 9,650,525 | B1 | 5/2017 | Suthar |
| 2004/0246327 | A1 | 12/2004 | Elzi |
| 2007/0279467 | A1 | 12/2007 | Regan |
| 2013/0158130 | A1* | 6/2013 | Heuer .................... A61K 8/731 514/772.1 |

FOREIGN PATENT DOCUMENTS

| | | |
|---|---|---|
| KR | 101655978 B1 | 9/2016 |
| WO | WO0160925 A3 | 12/2001 |
| WO | WO2009157928 A1 | 12/2009 |
| WO | WO2010027078 A1 | 3/2010 |
| WO | WO2011079402 A1 | 7/2011 |
| WO | WO2015134020 A1 | 9/2015 |
| WO | WO2015134024 A1 | 9/2015 |
| WO | WO2015134026 A1 | 9/2015 |
| WO | WO2015134027 A1 | 9/2015 |
| WO | WO2015134029 A1 | 9/2015 |
| WO | WO2017014747 A1 | 1/2017 |
| WO | 2017053178 A1 * | 3/2017 |
| WO | WO2017053178 A1 | 3/2017 |
| WO | 2017/100150 * | 6/2017 |
| WO | 2017100150 A1 * | 6/2017 |
| WO | WO2017100150 A1 | 6/2017 |

OTHER PUBLICATIONS

U.S. Appl. No. 16/262,965, filed Jan. 13, 2019, Bush, et al.
U.S. Appl. No. 16/262,967, filed Jan. 13, 2019, Lingoes, et al.
U.S. Appl. No. 16/262,970, filed Jan. 13, 2019, Lingoes, et al.

* cited by examiner

HETEROGENOUS COSMETIC INK COMPOSITION FOR INKJET PRINTING APPLICATIONS

FIELD OF THE INVENTION

Described herein is an ink composition for inkjet printing applications, and more particularly a cosmetic ink composition comprising a particulate material that exhibits controlled syneresis while still being suitable for high frequency printing via thermal and/or piezo inkjet printheads.

BACKGROUND OF THE INVENTION

For cosmetic printing applications, it is known that the ink must be sufficiently opaque to cover and/or hide skin imperfections. However, it is difficult to formulate an opaque stable ink which can be jetted due to the particle size and levels needed to achieve opacity. In addition, opaque inks can separate and exhibit settling of the large and/or dense particles used to create such inks. In particular, it is challenging to formulate an ink comprising titanium dioxide, a commonly used white pigment, that is printable via inkjet cartridges and/or printers. While there are multiple industries that routinely use titanium oxides in products which are stable, these products generally have very high viscosities. For instance, sunscreens and traditional makeups and/or skin care products which are applied manually comprise titanium oxide particles; however, they are only able to do so through viscosities that are orders of magnitude greater than the viscosity of typical inkjet compositions and are not compatible with inkjet printers and/or cartridges.

It was previously thought that inks should be homogenous prior to printing in order to avoid clogging of the microfluidic channels and to achieve consistent print quality (i.e. opacity). Current formulation approaches have utilized titanium oxides with a smaller particle size to slow the rate of separation and particle settling and/or have employed secondary particles such as hollow spheres to help provide some opacity. However, such formulations still separate within days or weeks and need to be homogenized before use. In addition, the opacity of these formulations is much lower than that of inks which use titanium oxides with particle sizes of 200 nm or greater. Other formulation approaches have utilized rheology modifiers and/or particle surface treatments to help slow the rate of separation and the particle settling. However, these inks need to be repeatedly agitated or recirculated to keep the ink homogeneous at the time of printing. In fact, manufacturers of such inks recommend vigorous shaking on a daily or weekly basis to homogenize the ink and/or recommend that these inks be recirculated during use. However, such interventions to homogenize the ink may not be compatible with consumer needs as these additional steps are inconvenient and may not be performed as instructed. In many instances, once an ink separates and the particles settle, it may no longer printable as it cannot be recovered even with vigorous and/or prolonged agitation.

As such, there is a need for an opaque inkjet ink composition that remains printable without intervention such as agitation or recirculation to meet the needs of consumer cosmetic applications. In particular, there is a need for a cosmetic ink composition that comprises particles that are big enough to create opacity yet remain uniformly suspended and has a viscosity that is compatible with inkjet printer cartridges and nozzle technology.

SUMMARY OF THE INVENTION

A cosmetic ink composition comprising: (a) a particulate material having a Particle Size Distribution D50 of from about 100 nm to about 2,000 nm; (b) polymeric dispersant having a weight average molecular weight of less than about 20,000 daltons; and (c) a polymeric rheology modifier; wherein the cosmetic ink composition has from about 0.1 to about 20 mm of separation after 11 days of static storage at 40° C., 1 atm, 60% relative humidity, in an 8-dram glass vial; wherein the separation is syneresis.

A cosmetic ink composition comprising: (a) from about 1 to about 30 active wt % of a particulate material comprising titanium dioxide; (b) a polymeric rheology modifier selected from the group consisting of alkali swellable emulsion polymers, hydrophobically modified alkali swellable emulsion polymers, and combinations thereof; (c) a polymeric dispersant having a weight average molecular weight of less than about 20,000 daltons; and (d) from about 10 to about 30 active wt % humectant; wherein when the cosmetic ink composition has from about 0.1 to about 20 mm of separation after 11 days at 25° C. of static storage at 40° C., 1 atm, 60% relative humidity, in an 8-dram glass vial; wherein the separation is syneresis.

An ink cartridge containing a cosmetic ink composition comprising: (a) from about 1 to about 30 active wt % titanium dioxide; (b) a polymeric dispersant having a weight average molecular weight of less than about 20,000 daltons; and (c) greater than about 0.3 active wt % of a polymeric rheology modifier selected from the group consisting of alkali swellable emulsion polymers, hydrophobically modified alkali swellable emulsion polymers, and combinations thereof; wherein the cosmetic ink composition has a Micro-CT Separation Value of from about 5% to about 50% after 28 days of static storage at 40° C., 1 atm, 75% relative humidity.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

DETAILED DESCRIPTION OF THE INVENTION

Figure 1:
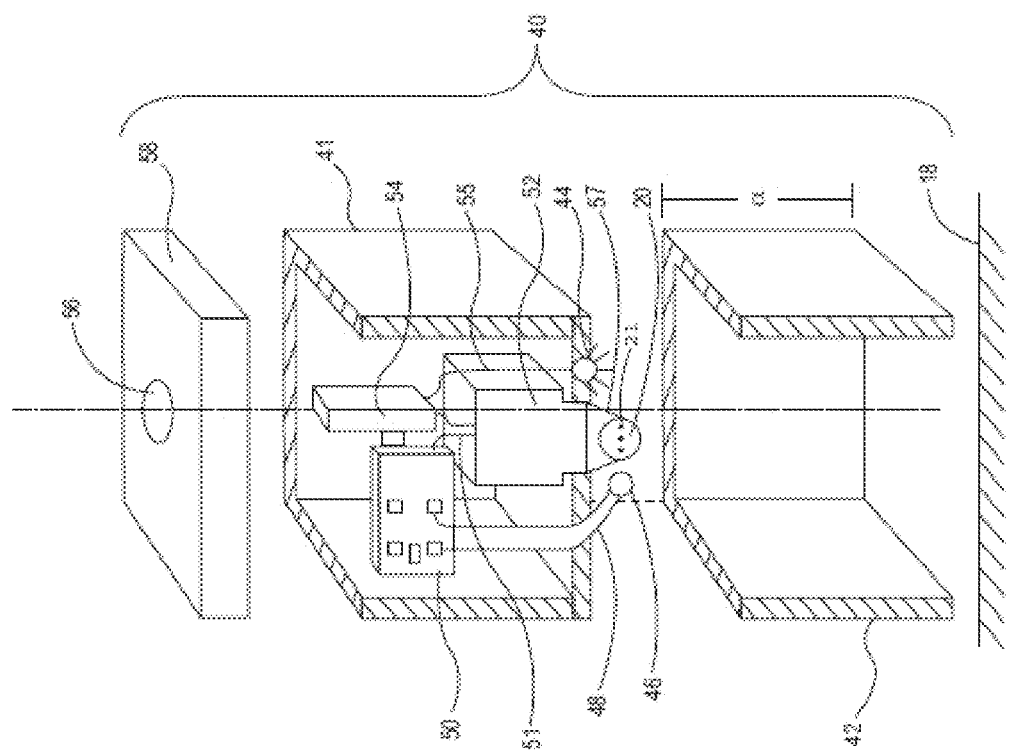
FIG. 1 is an exploded view of a personal care device for use in depositing the cosmetic ink composition described herein.

As used herein, "active wt %" and "wt % (active)" refers to the amount of solid of an ingredient dissolved or suspended in water in the composition.

As used herein, "ambient conditions" refers to a temperature of about 23 degrees Celsius (° C.) and 50% relative humidity (RH).

As used herein, "contrast ratio" refers to the opacity of the cosmetic ink composition, or the ability of the composition to reduce or prevent light transmission.

As used herein, "ink cartridge" refers to a body that defines a core and a die that contains one or more nozzles suitable for storing and printing ink compositions. An exemplary ink cartridge is described in US patent application Ser. No. US 2015/0359712.

As used herein, "Micro computed tomography (Micro-CT) Separation Value" refers to the percent of particle-lean, low viscosity phase relative to total cosmetic ink composition volume measured by micro-CT in the standpipe of an inkjet cartridge after static storage in the nozzles down cartridge orientation.

As used herein, "Particle Size Distribution D50" refers to the diameter where fifty percent of the distribution has a smaller particle size.

As used herein, "Particle Size Distribution D90" refers to the diameter where ninety percent of the distribution has a smaller particle size.

As used herein, "separation" refers to the formation of a second distinct phase in the sample regardless of the uniformity of the particles in the sample. Separation can include particle settling and/or syneresis.

As used herein, "settling" refers to the falling of particles in a composition due to gravity (according to Stokes' Law) to the bottom of a container. Particle settling can be affected by the size of the particles and their agglomeration over time.

As used herein, "static storage" refers to storage of a composition in the absence of vigorous or sustained vibration, agitation, or mixing prior to analysis or deposition of the composition.

As used herein, "syneresis" means phase separation, i.e. extraction or expulsion of a liquid from a gel, in this case a weak colloidal gel. The particles in a composition exhibiting syneresis are still uniformly suspended below the clear fluid layer.

As used herein, "polymeric dispersant to polymeric rheology modifier" refers to the ratio of the active wt % of the polymeric dispersant divided by the active wt % of the polymeric rheology modifier.

As used herein, "the storage modulus" or "G'" refers to the measure of the stored energy, representing the elastic portion of the composition.

As used herein, "the loss modulus" or "G''" refers to the measure of the energy dissipated as heat, representing the viscous portion of the composition.

As used herein, "weight percent as added" refers to the amount of the total active plus water as added to the composition.

As used herein, "zeta potential" refers to the electrokinetic potential of the cosmetic ink composition.

As used herein, the articles "a" and "an" are understood to mean one or more of the material that is claimed or described, for example, "a rheology modifier" or "an active".

All weights, measurements and concentrations herein are measured at ambient conditions unless otherwise specified.

All percentages, parts, and ratios as used herein are based upon the total weight of the cosmetic ink composition, unless otherwise specified. All such weights as they pertain to listed ingredients are based on the level as added in the composition, unless otherwise specified.

Cosmetic inks can require a white or light colored particulate material comprising particles large enough to be visually perceptible to the human eye in order to create opacity to cover skin imperfections. However, printing a cosmetic ink composition comprising a particulate material having a particle size large enough to be visually perceptible can be a challenge for current inks, printers, and/or cartridges. These challenges are caused primarily by separation and the settling of the large, dense particles and secondarily by the packing of the settled particles in the cartridge.

Current opaque inks are formulated to be printed within hours or days of preparation before separation and particle settling occurs. Other approaches create recoverable inks that can be homogenized using interventions like mixing, prolonged and/or vigorous agitation, and/or recirculation. Such inks may not be suitable for consumer in-home or hand-held printing purposes because their printable life is short and the vigorous and repeated agitation needed to keep the ink homogeneous is inconvenient. If the ink is not homogenized prior to printing, the particles can become irreversibly packed into the cartridge and/or the print opacity may not be consistent. Separation and settling can be minimized by adding rheology modifiers to the ink. However, if the viscosity of the cosmetic ink composition is not well controlled, clogging and the speed of flow through the microfluidic channels and nozzles can make printing difficult. The use of dispersants in cosmetic ink compositions may help control agglomeration (i.e. the sticking of particles to one another) and hard packing of the particles; however, such formulations still require intervention to homogenize the ink.

It was found that the combination of a polymeric rheology modifier and polymeric dispersant can suspend a particulate material having particles large enough to be visually perceptible, creating a heterogenous cosmetic ink composition that can be jettable without intervention. Careful balancing of the agglomeration of the particles and viscosity of the cosmetic ink composition can be used to create a heterogeneous cosmetic ink composition, while still being compatible with high frequency printing capabilities via thermal and/or piezo inkjet printheads.

It was found that the heterogenous cosmetic ink composition can undergo controlled syneresis, forming a weak colloidal gel phase and a particle-lean, low viscosity phase, which can be printed without interventions such as agitation, mixing, or re-circulation to homogenize the composition. The polymeric rheology modifier can build viscosity and create a colloidal gel which uniformly suspends the particles while the polymeric dispersant can prevent or limit the aggregation of the particles within the colloidal gel. The colloidal gel can be strong enough to hold the particles in suspension when not printing (thus inhibiting particle settling), but weak enough to break up during printing. Without being limited by theory, the particle-lean, low viscosity phase can be rich in solvent, such as water, and humectant, which are beneficial to nozzle health and recovery. It is believed that the particle-lean, low viscosity phase can help with printing startup by promoting nozzle health and preventing and/or improving nozzle clogging. One advantage to the cosmetic ink composition is that little to no shaking, and/or agitation of the composition by the consumer or automated mechanical processes before and/or during printing is needed to homogenize the ink. This can make the cosmetic ink composition more user-friendly as it does not require the consumer to perform an additional step to homogenize the ink and/or can eliminate the need for agitation or rotation systems, including automated systems, within the printing device, cartridge, printer servicing station, and/or docking station.

Described herein is a heterogeneous cosmetic ink composition that can exhibit long-term printability and a personal care device for depositing the cosmetic ink composition.

In one aspect, the cosmetic ink composition described herein can be jetted onto any surface, preferably a keratinous surface including human skin and/or hair.

In particular, it was found that a particulate material, such as $TiO_2$, a polymeric rheology modifier, such as alkali swellable emulsion ("ASE") polymers and hydrophobically modified alkali swellable emulsion ("HASE") polymers, and a polymeric dispersant can form a heterogeneous cosmetic ink composition that is jettable using standard cartridges and nozzles in a thermal and/or piezo printer without the need for intervention prior to or during printing. It was found that the cosmetic ink composition described herein can have from about 0.1 to about 25 mm of separation, wherein the separation is syneresis, as determined by the Separation Test Method described below, and can still be ejected from a cartridge. Additionally, it was found that inkjet cartridges filled with the cosmetic ink composition described herein can have a Micro-CT Separation Value of from about 5% to about 50%, alternatively from about 8% to about 30%, alternatively from about 10% to about 20%, after 28 days of static storage at 40° C., 1 atm, 75% relative humidity and are still printable. The Micro-CT-Separation Value can be measured according to the Micro-CT Separation Method described hereinafter.

In one aspect, the cosmetic ink composition need not be homogenized before and/or during use because the particles can remain in suspension in the gel phase over the shelf-life of the product, the particle-lean, low viscosity phase can promote nozzle health during startup, and the cosmetic ink composition can provide consistent printed opacity.

Cosmetic Ink Composition

In one aspect, the cosmetic ink composition can be a skin care composition. The cosmetic ink composition can hide or camouflage a skin imperfection, such as hyperpigmentation, when deposited precisely and substantially only onto the skin imperfection.

The cosmetic ink composition can be non-Newtonian, meaning the cosmetic ink composition can have a shear dependent viscosity and/or viscoelastic properties. The cosmetic ink composition can show shear thinning effects under the fluid ejection conditions in which the ink is moved between the cartridge and the printhead of an inkjet device. When the cosmetic ink composition is jetted, the shear rate can increase, resulting in a decrease in the viscosity. Thus, the cosmetic ink composition can exhibit syneresis during storage with the particles uniformly suspended in the gel phase, yet the viscosity and particle size are such that the cosmetic ink composition can still be printed.

The cosmetic ink composition can comprise a particulate material, a polymeric dispersant having a weight average molecular weight of less than about 20,000 daltons, and a polymeric rheology modifier.

In one aspect, the particulate material can be hydrophilic. In one aspect, the particulate material can be substantially coated with one or more ingredients to cause the particulate material to become more hydrophilic. As used herein, "substantially coated" can mean at least about 25%, preferably greater than about 50% surface coverage of the particulate material, more preferably greater than about 75%, most preferably greater than about 90%. Suitable coating ingredients that can render the particulate material hydrophilic in nature can include silica, alumina, polyethylene glycol (PEG) 12 dimethicone, phytic acid, sodium glycerophosphate, and combinations thereof. The particulate material can be substantially coated with one or more coating ingredients using techniques known in the art. One advantage to using a hydrophilic particulate material is that hydrophilic particulate material can be more easily dispersed in water. In one aspect, the particulate material can be titanium and/or iron oxide which has been substantially coated with silica and/or alumina.

Suitable particulate materials can include pigments; encapsulated pigments; mica; clay; mixed metal oxide pigments; metal oxides such as iron oxide, titanium dioxide, zinc oxide, aluminum hydroxide, iron oxide, and combinations thereof; boron nitride; silica; talc; basic lead carbonate; magnesium silicate; baryte ($BaSO_4$); calcium carbonate; pearlescent; colorants, including natural colorants and synthetic monomeric and polymeric colorants; dyes such as azo, indigoid, triphenylmethane, anthraquinone, and xanthine dyes which are designated as D&C and FD&C blues, browns, greens, oranges, reds, yellows, etc.; insoluble metallic salts of certified color additives, referred to as the Lakes; and combinations thereof.

In one aspect, the particulate material can comprise titanium dioxide, iron oxide, and combinations thereof. In one aspect, the titanium dioxide and/or iron oxide can be readily dispersed in water. In one aspect, the titanium dioxide and/or iron oxide is not hydrophobically treated before use in the cosmetic ink composition because it may not be readily dispersed in water. Suitable particulate material can include slurries of titanium dioxide and iron oxide available from KOBO Products Inc (South Plainfield, N.J.), or equivalents.

In one aspect, the cosmetic ink composition comprises a white pigment.

In one aspect, the cosmetic ink composition can have a white appearance. Alternatively, the cosmetic ink composition can have a white appearance with tints of red and/or yellow.

Typical levels of particulate material for sufficient opacity to hide and/or camouflage skin imperfections can be around 30 active wt %. In one aspect, the cosmetic ink composition can comprise greater than about 15 active wt % particulate material, alternatively greater than about 20 active wt %, alternatively greater than about 30 active wt %. In one aspect, the cosmetic ink composition can comprise from about 1 to about 30 active wt % particulate material, alternatively from about 3 to about 25 active wt %, alternatively from about 5 to about 20 active wt %, alternatively from about 8 to about 18 active wt %.

The particulate material can comprise particles having a Particle Size Distribution (PSD) D50 of about 100 nm to about 2,000 nm, alternatively from about 150 nm to about 1,000 nm, alternatively from about 200 nm to about 650 nm, alternatively from about 250 nm to about 350 nm. In one aspect, the particulate material can comprise particles having a PSD D90 of less than about 2 μm, alternatively less than about 1 μm. In one aspect, the particulate material can comprise particles having a PSD D90 of from about 700 nm to about 1250 nm, preferably from about 800 nm to about 900 nm. Without being limited by theory, it is believed that if the particles are too big, they can clog the microfluidic channels of the cartridge and disrupt printing. One skilled in the art would understand that an acceptable particle size can vary depending on printhead die architecture. In one aspect, the particulate material can comprise any PSD so long as the particles can move through the microfluidic channels of the cartridge and/or the printhead without causing clogging. The Particle Size Distribution can be measured according to the Particle Size Distribution Method described hereafter.

The particulate material can have a refractive index of between about 1.1 and about 5.0, alternatively from about 1.5 to about 4, alternatively from about 2 to about 3.

The particulate material can have a density range of from about 1.5 to about 6 g/mL, alternatively from about 2 to about 4 g/mL.

The cosmetic ink composition can comprise a polymeric rheology modifier. Polymeric rheology modifiers can assist in preventing settling by keeping the particles uniformly suspended such that little to no agitation of the cosmetic ink composition is needed.

One preferred group of polymeric rheology modifiers are ASE polymers. ASE polymers contain a balance of hydrophilic (meth)acrylic acid monomers and hydrophobic (meth)acrylate ester monomers and can be supplied at high volume solids in liquid form. ASE polymers rely on a change from low to high pH (neutralization) to trigger thickening. The "trigger" is built into the polymer by creating an approximately 50:50 ratio of (meth)acrylic acid, which is soluble in water, and a (meth)acrylate ester, which is not soluble in water. When the acid is un-neutralized (low pH), the polymer is insoluble in water and does not thicken. When the acid is fully neutralized (high pH), the polymer becomes soluble and thickens. ASE polymers are supplied at low pH (<5) and maintain a low as-supplied viscosity (<100 cP) at solids of up to 35%. When subject to a pH of about 7 or higher, ASE polymers solubilize, swell, and thicken the composition through volume exclusion. The degree of thickening can be related to the molecular weight of the polymer. Because their performance depends on water absorption and swelling, ASE polymers tend to be very high in molecular weight, which allows them to thicken efficiently. The rheology profiles ASE polymers create are typically steeply shear-thinning (pseudoplastic), and thus ASE polymers are well suited to build high viscosity at very low shear rates. Different rheological characteristics can be achieved by manipulating the molecular weight, as well as the types and amounts of acid and ester monomers, of the polymer.

In one aspect, the hydrophilic monomers of the ASE polymer can include (meth)acrylic acid and maleic acid. In one aspect, the hydrophobic monomers of the ASE polymer can include the esters of (meth)acrylic acid with $C_1$- to $C_4$-alcohols, in particular ethyl acrylate, butyl acrylate, and methyl methacrylate.

In one aspect, the ASE polymer can be synthesized from 10-90 wt % of Hydrophilic Monomer A and 10-90 wt % of Hydrophobic Monomer B. The structure of Hydrophilic Monomer A and Hydrophobic Monomer B are shown below.

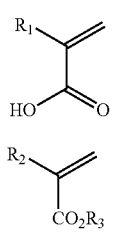

Hydrophilic Monomer A

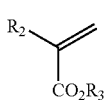

Hydrophobic Monomer B wherein $R_1$ and $R_2$ are independently hydrogen or methyl;
wherein $R_3$ is $C_1$ to $C_4$ alkyl.

Yet another group of polymeric rheology modifier suitable for use in the cosmetic ink composition described herein are HASE polymers. These are tertiary polymers that build on the ASE polymer chemistry by adding a hydrophobic acrylic ester and/or vinyl ester monomer to the polymer composition. HASE polymers retain the pH dependent behavior of their ASE counterparts, but in addition to absorbing water, HASE polymers also thicken via hydrophobe association. This mechanism, known as associative thickening (i.e. associating with any hydrophobic moiety in the composition), offers performance properties over a wider range of shear levels and enables a wider range of rheology profiles than is possible with volume exclusion thickeners such as ASE and cellulosic compositions.

The hydrophilic and hydrophobic monomers of the HASE polymers can be the same as described with respect to the ASE polymers. The associative monomer of the HASE polymer can be a monomer that shows a strong hydrophobic character. A preferred associative monomer is ester of (meth)acrylic acid with $C_8$-$C_{22}$ alcohols.

In one aspect, the HASE polymer can be synthesized from 10-90 wt % Hydrophilic Monomer A, 10-90 wt % Hydrophobic Monomer B, and 0.01 to 2 wt % Associative Monomer C. The structure of Associate Monomer C is shown below.

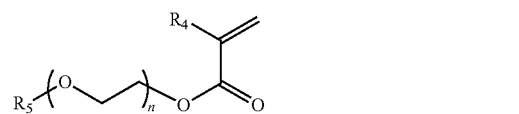

Associative Monomer C wherein $R_4$ is hydrogen or methyl;
wherein $R_5$ is $C_8$ to $C_{22}$ alkyl;
wherein n is an integer from 0 to 50.

Alternatively, the HASE polymer can be synthesized from 10-90 wt % Hydrophilic Monomer A, 10-90 wt % Hydrophobic Monomer B, and 0.01 to 2 wt % Associative Monomer D. The structure of Associative Monomer D is shown below.

Associative Monomer D wherein $R_6$ is hydrogen or methyl;
wherein $R_7$ is $C_8$ to $C_{22}$ alkyl.

In one aspect, the associative monomer can be selected from the group consisting of steareth-20 methacrylate, beheneth-25 methacrylate, vinyl neodecanoate, and combinations thereof. In one aspect, more than one associative monomers can be used in the synthesis of the HASE polymer.

In one aspect, ASE and HASE polymers can comprise a cross-linking agent. The cross-linking agent can contain at least two ethylenically unsaturated moieties, alternatively at least three ethylenically unsaturated moieties. Suitable cross-linking agents can include divinyl benzene, tetra allyl ammonium chloride, allyl acrylates, methacrylates, diacrylates, dimethacrylates of glycols and polyglycols, butadiene, 1,7-octadiene, allyl-acrylamides, allyl-methacrylamides, bisacrylamidoacetic acid, N, N'-methylene-bisacrylamide, polyol polyallylethers such as polyallylsaccharose and pentaerythrol triallylether, and mixtures thereof.

In one aspect, the cross-linking agent can be present at a level of from about 25 to about 5,000 ppm, alternatively from about 50 to about 1,000 ppm, alternatively from about 100 to about 500 ppm.

Another group of polymeric rheology modifiers are hydrophobically-modified ethylene oxide-based urethane (HEUR) polymers. Unlike ASE or HASE-type rheology modifiers, HEUR polymers are non-ionic and soluble at any pH. This solubility is due to the polymer's ethylene oxide backbone, which is water soluble and makes up the majority of the polymer structure. Thus, HEUR polymers require a hydrophobic moiety in the composition to interact with the ethylene oxide backbone to impart structure. The cosmetic ink composition can comprise a HEUR polymer. Alternatively, the cosmetic ink composition comprises little to no hydrophobic moieties and does not comprise a HEUR polymer.

The polymeric rheology modifier can be a (meth)acrylate polymer, a (meth)acrylate copolymer, and mixtures thereof. The polymeric rheology modifier can be selected from the group consisting of ASE polymers, HASE polymers, and combinations thereof. Suitable HASE polymers can include ACULYN™ Excel; ACRYSOL™ TT615; ACULYN™ 22; ACULYN™ 88; (all available from The DOW Chemical Company, Lake Zurich, Ill.); and combinations thereof. Suitable ASE polymers can include Rheovis® 1125 (available from BASF Corporation, Charlotte, N.C.), ACULYN™ 33; ACULYN™ 38 (both available from The DOW Chemical Company, Lake Zurich, Ill.); and combinations thereof. The cosmetic ink composition can comprise an ASE polymer. Alternatively, the cosmetic ink composition can comprise an HASE polymer.

Other suitable polymeric rheology modifiers can include bioderived polymers such as starches and gums. Starches may be sourced from corn, wheat, potato, rice, cassava, tapioca, and combinations thereof. Starches may be unmodified, modified, or partially degraded. Modified starch may include cationic starch, hydroxyethyl starch, carboxymethylated starch, polylactic acid graft-starch, polycaprolactone graft starch, and combinations thereof. Degraded starches may include dextrin and maltodextrin, preferably with a dextrose equivalent of 30 or lower. Gums can be extracted from natural sources, modified from natural sources, or fermented. Suitable natural sources of gums can include trees, plants, animals, and seeds. Examples of natural gums can include gum acacia, gum tragacanth, gum karaya, gum ghatti, nanocrystalline cellulose, pectin, carrageenan, agar, furcellaran, konjac gum, gelatin, guar gum, locast bean gum, tara gum, cassia gum, mesquite gum, tamarind seed gum, quince seed gum, flaxseed gum, psyllium seed gum, oat gum, microfibrillated cellulose, and combinations thereof. Gums may also be modified to create alkali cellulose, salts of carboxymethylcellulose, methylcellulose, hydroxypropyl methylcellulose, hydroxypropyl cellulose, and hydroxyethyl cellulose. Examples of fermented gums are xanthan gum, dextran, pullulan, and combinations thereof.

The polymeric rheology modifier does not consist of a molecular rheology modifiers such as surfactants or amine oxides.

The cosmetic ink composition can comprise any amount of polymeric rheology modifier so long as the first dynamic viscosity of the cosmetic ink composition is greater than about 1,100 cP at a shear rate of 0.1 sec$^{-1}$ measured at 25° C. The cosmetic ink composition can comprise greater than about 0.30 active wt % rheology modifier, alternatively greater than about 0.40 active wt %, alternatively greater than about 0.50 active wt %. The cosmetic ink composition can comprise from about 0.30 to about 1 active wt % rheology modifier, alternatively from about 0.30 to about 0.80 active wt %, alternatively from about 0.40 to about 0.50 active wt %. Active wt % can be measured using standard High Performance Liquid Chromatography-Mass Spectrometry (HPLC-MS) techniques. One advantage to keeping the level of rheology modifier within this range is that the viscosity of the cosmetic ink composition can be built such that the particles can be suspended in the composition. The particles can be suspended for about 11 days or more at 25° C., alternatively about 30 days or more at 25° C., alternatively for about 90 days or more at 25° C., alternatively for about 300 days or more at 25° C. Without being limited by theory, it is believed that at levels of rheology modifier below this range the particles may not be sufficiently suspended and settling may occur. If the level of rheology modifier is too high, the viscosity of the cosmetic ink composition may increase to a point that can impact jetting (i.e. the cosmetic ink composition may not shear thin enough for efficient printing).

In one aspect, the cosmetic ink composition can be substantially free of neutral inorganic salts (as compared to an alkali salt base, like NaOH). Without being limited by theory, it is believed that neutral inorganic salts, such as calcium chloride or sodium chloride, can increase the ionic strength of the cosmetic ink composition and can disrupt the internal structure, thus impacting stability. It is known that HASE and/or ASE polymers become polyelectrolytes at high pHs. As pH increases, the carboxylic acids on the HASE and/or ASE polymers can be neutralized, generating ionic groups on the polymer chains that can produce electrostatic repulsion. These electrostatic repulsions can cause the polymer to expand and form an internal structure in the composition. It is believed that inorganic neutral salts can shield this electrostatic repulsion and can cause the HASE and/or ASE polymer to change structure, and thus its effectiveness in promoting stability.

The cosmetic ink composition can comprise a polymeric dispersant. The polymeric dispersant can be a low molecular weight linear or branched homopolymer or copolymer that can act to control particle size and can help maintain a low viscosity in the cosmetic ink composition. The polymeric dispersant does not greatly increase viscosity of the cosmetic ink composition. Examples of polymeric dispersants that can be used herein can include polymers obtained from one or more hydrophilic monomers and optionally hydrophobic monomers.

Non-limiting examples of hydrophilic monomers can include styrene sulfonic acid; ALPHA, BETA-ethylenically unsaturated carbonic acid; derivatives of ALPHA, BETA-ethylenically unsaturated carbonic acid; acrylic acid; derivatives of acrylic acid; methacrylic acid; derivatives of methacrylic acid; maleic acid; derivatives of maleic acid; itaconic acid; derivatives of itaconic acid; fumaric acid; derivatives of fumaric acid; and combinations thereof.

Non-limiting examples of hydrophobic monomers can include styrene; derivatives of styrene; vinyltoluene; derivatives of vinyltoluene; vinylnaphthalene; derivatives of vinylnaphthalene; butadiene; derivatives of butadiene; isoprene; derivatives of isoprene; ethylene; derivatives of ethylene; propylene; derivatives of propylene; alkyl esters of acrylic acid; alkyl esters of methacrylic acid; and combinations thereof.

The polymeric dispersant may also comprise a monomer selected from the group consisting of a polyoxyethylene group, a hydroxyl group, acrylamide, acrylamide derivatives, dimethylaminoethyl methacryate, ethoxyethyl methacrylate, butoxyethyl methacrylate, ethoxytriethylene methacrylate, methoxypolyethyleneglycol methacrylate, vinylpyrrolidone, vinylpyridine, vinylalcohol, alkylethers any salts thereof, and combinations thereof.

The polymeric dispersant may be in the acid form. The polymeric dispersant can be a salt of the acid form. Non-limiting examples of salts can include onium compounds of hydrogen, alkali metals, ammonium ion, organic ammonium ion, phosphonium ion, sulfonium ion, oxonium ion, stibonium ion, stannonium ion, iodonium ion, other onium ions, and combinations thereof.

In one aspect, the polymeric dispersant can be a polyacrylic acid or a salt thereof, such as sodium, potassium, ammonium, and mixtures thereof. In one aspect, the polymeric dispersant can be sodium polyacrylate such as Darvan® 811D (available from RT Vanderbilt Holding Company Inc., Norwalk, Conn.), ammonium polyacrylate having a weight average molecular weight of about 3,500 daltons such as Darvan® 821A (available from RT Vanderbilt Holding Company Inc.), and combinations thereof.

The polymeric dispersant can have a weight average molecular weight of less than about 20,000 daltons, preferably less than about 10,000 daltons, more preferably less than about 5,000 daltons. The cosmetic ink composition can comprise a polymeric dispersant having a weight average molecular weight of from about 1,000 to about 20,000 daltons, alternatively from about 1,000 to about 10,000 daltons, alternatively from about 2,000 to about 5,000 daltons, alternatively from about 2,500 to about 4,000 daltons. Weight average molecular weight can be measured by standard High Performance Size-Exclusion Chromatography per ASTM method D5296-11 (Sep. 1, 2011).

In one aspect, the polymeric dispersant is not a film forming polymer. Without being limited by theory it is believed that the polymeric dispersant will not form a film because of the low molecular weight.

The cosmetic ink composition can comprise from about 0.01 to about 1 active wt % polymeric dispersant, alternatively from about 0.10 to about 0.85 active wt %, alternatively from about 0.20 to about 0.75 active wt %, alternatively about 0.30 to about 0.65 active wt %. Without being limited by theory, it is believed that the polymeric dispersant can control agglomeration, and thus the particle size, of the particulate material by creating a negative surface charge around the particles. Thus, the polymeric dispersant can help to maintain a particle size that is compatible with printer cartridges and nozzles. Without being limited by theory, it is believed that a cosmetic ink composition comprising below 0.01 active wt % polymeric dispersant may not have sufficient particle size control and/or the viscoelastic modulus may be too high to allow for reliable refill of the microfluidics.

The ratio of the polymeric dispersant to the polymeric rheology modifier can be less than about 1. The ratio of polymeric dispersant to polymeric rheology modifier can be from about 0.10 to about 0.75, alternatively from about 0.30 to about 0.65. Without being limited by theory it is believed that if the level of polymeric dispersant is greater than the level of polymeric rheology modifier, the polymeric rheology modifier may not be able to build the internal structure needed to suspend the particles. If the ratio of polymeric dispersant to polymeric rheology modifier is too low, agglomeration may not be well controlled and the particle size may become too large to fit through printer nozzles, making printing difficult.

It is believed that stability is inversely proportional to the level of polymeric dispersant and directly proportional to the level of polymeric rheology modifier.

The cosmetic ink composition can have a first dynamic viscosity of greater than about 1,100 cP at a shear rate of 0.1 $sec^{-1}$ measured at 25° C. and a second dynamic viscosity of less than about 100 cP at a shear rate of 1,000 $sec^{-1}$ measured at 25° C. The cosmetic ink composition can have a first dynamic viscosity of from about 1,100 cP to about 10,000 cP at a shear rate of 0.1 $sec^{-1}$ at 25° C., alternatively from about 1,500 cP to about 8,000 cP, alternatively from about 2,000 cP to about 5,000 cP. The cosmetic ink composition can have a second dynamic viscosity of from about 10 cP to about 100 cP at a shear rate of 1,000 $sec^{-1}$ at 25° C., alternatively from about 20 to about 80 cP. Without being limited by theory, it is believed that a shear rate of 0.1 $sec^{-1}$ can be representative of storage conditions, while a shear rate of 1,000 $sec^{-1}$ can be representative of printing conditions. Viscosity can be measured according to the Viscosity Test Method described hereinafter. One advantage to having a first and second dynamic viscosity in this range is that at high shear rate, the cosmetic ink composition can drop to a viscosity that is similar to Newtonian inks, yet can still maintain a viscosity sufficient to suspend the particles when not printing.

The cosmetic ink composition can have a first dynamic viscosity measured at a shear rate of 0.1 $sec^{-1}$ at 25° C. that is about 70% higher than the second dynamic viscosity of the cosmetic ink composition when measured at a shear rate of 1,000 $sec^{-1}$ at 25° C., alternatively about 80% higher, alternatively about 90% higher, alternatively about 95% higher. The cosmetic ink composition can have a first dynamic viscosity measured at a shear rate of 0.1 $sec^{-1}$ at 25° C. that is about 25 times greater than the second dynamic viscosity of the cosmetic ink composition when measured at a shear rate of 1,000 $sec^{-1}$ at 25° C., alternatively about 35 times greater, alternatively about 50 times greater, alternatively about 80 times greater.

The cosmetic ink composition can have temperature dependent viscosity. Lower viscosity was observed at a shear rate of 1000 $sec^{-1}$ at an elevated temperature of about 70° C.

The cosmetic ink composition can have a storage modulus (G') of from about 2 to about 10, alternatively from about 3 to about 8, alternatively from about 4 to about 6. Without being limited by theory, it is believed that if the G' of the cosmetic ink composition is greater than about 10, the decap or start up after idle time in the printhead may be difficult without intervention because the composition is too elastic. Storage modulus can be measured according to the Oscillatory Strain Sweep Method described hereafter.

The cosmetic ink composition can have a loss modulus (G") of from about 1 to about 5, alternatively from about 1.5 to about 4, alternatively from about 2 to about 3. Loss modulus can be measured according to the Oscillatory Strain Sweep Method described hereafter.

The ratio of loss modulus to storage modulus, or tan (delta), is a useful representation of the extent of elasticity in a fluid. In this case, it can be a measure of the intrinsic stability of the cosmetic ink composition. When G" is higher than G', tan(delta) is greater than about 1 and indicates a viscous dominant fluid behavior. When G' is higher than G", tan(delta) is less than about 1 and indicates an elastic dominant fluid behavior.

The cosmetic ink composition can have a tan(delta) of about 1. Alternatively, the cosmetic ink composition can have a tan(delta) of less than about 1, alternatively less than about 0.6. Without being limited by theory it is believed that when the tan(delta) is less than about 0.6, particle settling can be minimized and/or prevented. The cosmetic ink composition can have a tan(delta) of from about 0.2 to about 1, alternatively from about 0.4 to about 0.9, alternatively from about 0.6 to about 0.8.

The cosmetic ink composition can have a zeta potential of about negative 20 or less, alternatively about negative 30 or less, alternatively greater than about positive 20, alternatively greater than about positive 30. The cosmetic ink composition can have a zeta potential of about negative 20 or less, or greater than about positive 20. One advantage to having a zeta potential in this range is that the surface charge of the particles can be increased, thus preventing agglomeration of the particles. Zeta potential can be measured according to the Zeta Potential Test Method described hereafter.

The cosmetic ink composition can have a neat pH of greater than about 7.5. The cosmetic ink composition can have a neat pH of about 7.5 to about 9.0, alternatively from about 7.5 to about 8.5. Without being limited by theory, it is believed that at a pH lower than about 7.5, syneresis can occur at a faster rate. It is believed that at a lower pH, the equilibrium between the carboxylic acid and carboxylate salts of the rheology modifier can be pushed toward the protonated acid and therefore are not available to suspend the particles. It is believed that as the pH increases, the larger the negative zeta potential becomes, thus preventing agglomeration of the particles. The cosmetic ink composition can comprise a buffering agent for adjusting the pH conditions. The buffering agent can be any basic excipient. In one aspect, the buffering agent can be a strong base, such as sodium hydroxide, potassium hydroxide, calcium hydroxide, and mixtures thereof. The neat pH of the cosmetic ink composition can be measured by standard methodology known to those skilled in the art.

The cosmetic ink composition can have a surface tension of from about 25 to about 60 dyn/cm, alternatively from about 30 to about 55 dyn/cm, alternatively from about 40 to about 50 dyn/cm.

The cosmetic ink composition can have an opacity of at least 0.2. In one aspect, the cosmetic ink composition can comprise an opacity of from about 0.2 to about 1, alternatively from about 0.25 to about 0.8, alternatively from about 0.3 to about 0.5.

The cosmetic ink composition can be substantially free of particle settling. Substantially free of particle settling can mean that the variation between the weight % solids of the top and bottom of a sample of the cosmetic ink composition is less than 5% at ambient conditions at 4 days after formulation, alternatively less than about 3%, alternatively less than about 1%. Particle settling can be measured according to the Particle Settling Test Method described hereafter.

The cosmetic ink composition can be substantially free of particle agglomeration. Substantially free of particle agglomeration can mean that the cosmetic ink composition exhibits less than about 25 nm of particle growth per month at ambient conditions, alternatively less than about 15 nm, alternatively less than about 10 nm. The rate of agglomeration can be determined by measuring particle size according to the Particle Size Distribution method described hereafter over a period of time.

The cosmetic ink composition can have from about 0.1 to about 20 mm of separation after 11 days of static storage at 40° C., 1 atm, 60% relative humidity, in an 8-dram glass vial, wherein the separation is syneresis, alternatively from about 0.5 to about 15 mm, alternatively from about 1 to about 10 mm, alternatively from about 1.5 to about 5 mm. The amount of separation can be measured according to the Separation Test Method described hereafter.

When the cosmetic ink composition is deposited from an inkjet and/or piezo printer, the deposited titanium dioxide solids content is from about 10% to about 25% after static storage for 30 days at 40° C., 1 atm, 75% relative humidity. Deposited titanium dioxide solids content can be determined by Thermogravimetric Analysis.

When the cosmetic ink composition is deposited from an inkjet and/or piezo printer after static storage for 30 days at 40° C., 1 atm, 75% relative humidity, the average printed contrast ratio after 40 print cycles is about 20% or more.

The cosmetic ink composition can have a shelf-life of about 1 month, alternatively about 3 months, alternatively about 6 months, alternatively about 12 months, alternatively about 18 months, alternatively about 24 months. As used herein, "shelf-life" means the amount of time at ambient conditions that the cosmetic ink composition remains jettable without the need for shaking or agitation.

The cosmetic ink compositions may further comprise a humectant as a carrier or chassis for the other components in the cosmetic ink composition. An exemplary class of humectants can include polyhydric alcohols. Suitable polyhydric alcohols can include polyalkylene glycols and alkylene polyols and their derivatives, including propylene glycol, dipropylene glycol, polypropylene glycol, polyethylene glycol and derivatives thereof; sorbitol; hydroxypropyl sorbitol; erythritol; threitol; pentaerythritol; xylitol; glucitol; mannitol; butylene glycol (e.g., 1,3-butylene glycol); pentylene glycol; hexane triol (e.g., 1,2,6-hexanetriol); glycerin; ethoxylated glycerine; propoxylated glycerine; and mixtures thereof.

Other suitable humectants can include sodium 2-pyrrolidone-5-carboxylate; guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); hyaluronic acid and derivatives thereof (e.g., salt derivatives such as sodium hyaluronate); lactamide monoethanolamine; acetamide monoethanolamine; urea; sodium pyroglutamate, water-soluble glyceryl poly(meth)acrylate lubricants (such as Hispagel®, available from BASF, Ludwigshafen, Germany); and mixtures thereof.

The cosmetic ink composition can comprise from about 1 to about 40 active wt % humectant, alternatively from about 5% to about 35%, alternatively from about 10% to about 30%, alternatively from about 15% to about 20%. Alternatively, the cosmetic ink composition can comprise from about 20 to about 30 active wt % humectant.

Without being limited by theory, it is believed that at a level of about 20 active wt % or more the humectant can help prevent drying and/or clogging of the nozzles and/or cartridge when the cosmetic ink composition is not being printed.

In one aspect, the level of humectant is less than about 30 active wt % to promote fast dry times of the cosmetic ink composition on the skin.

The cosmetic ink composition can be delivered alone or in the presence of a dermatologically-acceptable carrier. The phrase "dermatologically-acceptable carrier", as used herein, means that the carrier is suitable for topical application to a keratinous tissue, has good aesthetic properties, is compatible with any additional components of the cosmetic ink composition, and/or will not cause any untoward safety or toxicity concerns. In one aspect, the cosmetic ink composition is safe for use on skin. In one aspect, the cosmetic ink composition does not comprise alkyds, formaldehydes, phenolics, ketones, rubber resins, and combinations thereof because such ingredients may not be compatible with use on human skin. In one aspect, the cosmetic ink composition can be hypoallergenic. Water is by far the most common carrier, and is typically used in combination with other carriers. The carrier can be in a wide variety of forms. Non-limiting examples include simple solutions (water or oil based) or emulsions. The dermatologically acceptable carrier can be in the form of an emulsion. Emulsion may be generally classified as having a continuous aqueous phase (e.g., oil-in-water and water-in-oil-in-water) or a continuous oil phase (e.g., water-in-oil and oil-in-water-in-oil). The oil phase may comprise silicone oils, non-silicone oils such as hydrocarbon oils, esters, ethers, and the like, and mixtures thereof. For example, emulsion carriers can include, but are not limited to, continuous water phase emulsions such as silicone-in-water, oil-in-water, and water-in-oil-in-water emulsion and continuous oil phase emulsions such as water-in-oil and water-in-silicone emulsions, and oil-in-water-in-silicone emulsions.

The cosmetic ink composition can comprise water, preferably deionized water. The cosmetic ink composition can comprise from about 40% to about 75% water, by weight of the cosmetic ink composition, alternatively from about 55% to about 70%, alternatively from about 60% to about 68%.

Additionally, the cosmetic ink composition can optionally include anti-fungal and/or anti-bacterial components.

The cosmetic ink composition can optionally comprise a preservative. Non-limiting examples of suitable preservatives can include phenoxy ethanol, 1,2-Hexanediol, 1,2-Octanediol (commercially available as SymDiol® 68 from Symrise, AG, Branchburg, NJ), farnesol, 2-methyl 5-cyclohexypentanol, 1,2-decanediol, and combinations thereof. The cosmetic ink composition can comprise from about 0.01% to about 10% preservative, alternatively from about 0.1% to about 5%, alternatively from about 1% to about 3%, all by weight of the cosmetic ink composition. One advantage to including a preservative is that it can help to prevent microbial growth in the cosmetic ink composition, for instance if the cosmetic ink composition becomes contaminated with bacteria from the skin.

The cosmetic ink composition may comprise a monohydric alcohol. The cosmetic ink composition can comprise about 50 ppm or more of a monohydric alcohol. The cosmetic ink composition can comprise from about 50 to about 10,000 ppm of a monohydric alcohol, alternatively from about 100 to about 5,000 ppm, alternatively from about 100 to about 1,000 ppm. Suitable monohydric alcohols include methanol, ethanol, 1-propanol, 2-propanol, 1-butanol, 2-butanol, 2-methyl-1-propanol and 2-methyl-2-propanol.

The cosmetic ink composition may comprise a safe and effective amount of one or more skin care actives ("active") useful for regulating and/or improving the skin. "Safe and effective amount" means an amount of a compound or composition sufficient to induce a positive benefit but low enough to avoid serious side effects (i.e., provides a reasonable benefit to risk ratio within the judgment of a skilled artisan). A safe and effective amount of an active can be from about $1\times10^{-6}$ to about 25%, alternatively from about 0.0001 to about 20%, alternatively from about 0.01 to about 10%, alternatively from about 0.1 to about 5%, alternatively from about 0.2 to about 2%, all by weight of the cosmetic ink composition.

Suitable skin care actives include, but are not limited to, vitamins (e.g., B3 compounds such as niacinamide, niacin-nicotinic acid, and tocopheryl nicotinate; B5 compounds such as panthenol; vitamin A compounds and natural and/or synthetic analogs of Vitamin A, including retinoids, retinol, retinyl acetate, retinyl palmitate, retinoic acid, retinaldehyde, retinyl propionate, and carotenoids (pro-vitamin A); vitamin E compounds, or tocopherol, including tocopherol sorbate and tocopherol acetate; vitamin C compounds, including ascorbate, ascorbyl esters of fatty acids, and ascorbic acid derivatives such as magnesium ascorbyl phosphate and sodium ascorbyl phosphate; ascorbyl glucoside; and ascorbyl sorbate); peptides (e.g., peptides containing ten or fewer amino acids, their derivatives, isomers, and complexes with other species such as metal ions); sugar amines (e.g., N-acetyl-glucosamine); sunscreens; oil control agents; tanning actives; anti-acne actives; desquamation actives; anti-cellulite actives; chelating agents; skin lightening agents; flavonoids; protease inhibitors (e.g., hexamidine and derivatives); non-vitamin antioxidants and radical scavengers; salicylic acid; hair growth regulators; anti-wrinkle actives; anti-atrophy actives; minerals; phytosterols and/or plant hormones; tyrosinase inhibitors; N-acyl amino acid compounds; inositol; undecylenoyl phenylalanine; moisturizers; plant extracts; and derivatives of any of the aforementioned actives; and combinations thereof. The term "derivative" as used herein refers to structures which are not shown but which one skilled in the art would understand are variations of the basic compound. For example, removing a hydrogen atom from benzene and replacing it with a methyl group.

In one aspect, the cosmetic ink composition can comprise peroxide, including hydrogen peroxide and/or benzoyl peroxide.

In one aspect, the cosmetic ink composition can comprise a skin care active selected from the group consisting of niacinamide; inositol; undecylenoyl phenylalanine; and combinations thereof.

In one aspect, the cosmetic ink composition is substantially free of latex polymer binders and/or a film forming polymers. In one aspect, the cosmetic ink composition comprises less than about 10% latex polymer binders and/or film forming polymers, alternatively less than about 1%, alternatively less than about 0.1%. Without being limited by theory, it is believed that latex polymer binders and/or film forming polymers can make printing can be difficult because these polymers can solidify after evaporation and irreversibly plug the nozzles.

In one aspect, the cosmetic ink composition comprises from about 10% to about 30% solids. In one aspect, the cosmetic ink composition comprises less than 40% solids. Without being limited by theory, it is believed that at a solids level of greater than 40%, such as in prepaints or paints, printing can be difficult because a high level of solids may lead to irreversible nozzle clogging.

In one aspect, the cosmetic ink composition can be removeable with water, alternatively with soap and water.

Personal Care Device

In one aspect, the cosmetic ink composition described herein can be applied to the skin using a hand-held personal care device. The personal care device can analyze the skin, identify skin imperfections, and deposit the cosmetic ink composition onto the identified skin imperfection in order to hide and/or camouflage the skin imperfection. An exemplary personal care device is described in U.S. Pat. No. 9,522,101.

In one aspect, the personal care device can comprise a sensor configured to take at least one image of skin and a processor configured to calculate the average background lightness value of the image on a grey scale (lightness value on a grey scale is herein referred to as "L value"). Further, from the same image, a local L value can be calculated for individual pixels or a group of pixels. The processor can then compare the local L value to the background L value to identify skin imperfections.

When a skin imperfection is identified, the processor can activate one or more nozzles to fire and dispense the cosmetic ink composition onto the skin imperfection.

A skin imperfection is an area of skin where the absolute value of the difference between a local L value and the background L, this difference being defined as the measured delta L ("$\Delta L_M$"), is greater than a predetermined set delta L ("$\Delta L_S$"). The background L can be preset or calculated anywhere within the image. The image can be taken where the nozzles will fire the cosmetic ink composition. The background L can be the arithmetic average, median, or mean of a plurality of local Ls, which means the calculation can include all of the local Ls in the image, or a subset thereof.

FIG. 1, shows an exploded view of personal care device 40. Physical spacer 42 of personal care device 40 is directly above skin surface 18. Physical spacer 42 has a set, predetermined height a such that when it contacts skin surface 18, the mechanical and electrical elements are all at a known distance from skin surface 18. In one aspect, the height αis from about 1 mm to about 20 mm, alternatively from about 3 mm to about 15 mm, alternatively from about 4 mm to about 10 mm.

The mechanical and electrical elements associated with personal care device 40 can include, but are not be limited to, light 44, sensor 46, nozzle array 20 which is embedded on cartridge die 57 which is attached to cartridge 52. Cartridge die 57 can be made of silicon, glass, machinable glass ceramic, sapphire, alumina, printed wiring board substrates (for example, Liquid Crystal Polymer, polyimide etc.) within which nozzle array 20 can be formed. Nozzle array 20 can be in a linear configuration, multiple rows, off-set, sine wave, curved, circular, saw tooth arrangements, and combinations thereof. All of these elements can be enclosed within optional apparatus housing 41.

Light 44 can illuminate the area of skin surface 18 within physical spacer 42 such that sensor 46 has relatively constant illumination. Background lighting can affect sensor 46 as portions of physical spacer 42 lift off skin surface 18 and allow background light in and the illumination from light 44 to escape. Small deviations in illumination can be corrected for provided light 44 provides a relatively constant background illumination. In one aspect, physical spacer 42 can be opaque. Light 44 can be a LED, incandescent light, neon bulb based, or any other commercially available source of illumination. Light 44 can have constant illumination or adjustable illumination. For example, an adjustable light source might be useful if the background illumination is excessively bright or dark.

Sensor 46 can be any component that is capable of obtaining a visual property of an area of skin surface. Non-limiting examples of sensors can include optical sensors, image capture devices, spectrophotometers, photonic measuring devices for wavelengths within the visible spectrum as well as those wavelengths above and below the visible spectrum which could measure sub-surface features, and combinations thereof. The image capture device can be any of a variety of commercially available devices such as a simple camera or a digital cmos camera chip. In one aspect, the image capture device can be a camera and the images can be taken or converted to a standard grey scale that is known in the art. It is understood that any numerical scale that measures lightness to darkness can be considered a "grey scale". Moreover, as used herein, "grey scale" is intended to be a linear scale, or one band, or one visual attribute. For example, one "grey scale" visual attribute could be single wavelength or a narrow wavelength to define a specific visual color. Another example of one "grey scale" visual attribute could be a mix of wavelength numerical values averaged for each pixel making up the image, such as a true black, grey or white image from an RGB mixture.

Sensor 46 can take a measurement of the L value of skin surface 18 and/or an image of skin surface 18 and can send it to processor 50 via image capture line 48 for analysis. The image may be analyzed for local L values, background L values, or both. Grey scale conversion can occur within the analytical processing capabilities of processor 50. The comparison of background L to local L to determine the $\Delta L_M$ occurs within processor 50, which can be a commercially available programmable chip, or other commercially available processing units.

Processor 50 is generally referred to as a central processing unit ("CPU"). The CPU can be a single programmable chip like those found in consumer electronic devices such as a laptop computer, a cell phone, an electric razor, and the like. The CPU may comprise an Application Specific Integrated Circuit (ASIC), controller, Field Programmable Gate Array (FPGA), integrated circuit, microcontroller, microprocessor, processor, and the like. The CPU may also comprise memory functionality, either internal to the CPU as cache memory, for example Random Access Memory (RAM), Static Random Access Memory (SRAM), and the like, or external to the CPU, for example as Dynamic Random-Access Memory (DRAM), Read Only Memory (ROM), Static RAM, Flash Memory (e.g., Compact Flash or SmartMedia cards), disk drives, Solid State Disk Drives (SSD), or Internet Cloud storage. While it is anticipated that a remote CPU, either tethered to the personal care device or which communicates wirelessly, can be used, a local CPU within the personal care device is exemplified herein.

Images can be taken in sequence or preferably continuously. The image capture device can take images at a speed of at least 4 frames per second, alternatively at least 100 frames per second, alternatively at least 200 frames per second, alternatively at least 600 frames per second.

The CPU can process at a rate of 100 frames per second, alternatively greater than 200 frames per second, alternatively greater than 600 frames per second.

The results of the image analysis, when compared to criteria pre-programmed into processor 50, may result in a desired treatment of skin surface 18. For instance, when the calculated $\Delta L_M$ exceeds the pre-determined $\Delta L_S$, a signal is sent from processor 50 to cartridge 52, via cartridge line 51, to fire one or more nozzles 21 in nozzle array 20 and dispense the cosmetic ink composition.

Power for cartridge 52, light 44, sensor 46, processor 50, and other mechanical and electrical elements that might be present can be supplied by power element 54 via one or more power lines 55. Power element 54 can be turned off and on, which in turn turns personal care device 40 off and on, via power switch 56 which can be located anywhere on personal care device 40, but is shown here on device cover 58. Power element 54 may include energy storage functionality via a battery, a rechargeable battery, an electrochemical capacitor, a double-layer capacitor, a supercapacitor, a hybrid battery-capacitor system, and combinations thereof.

Figure 2:
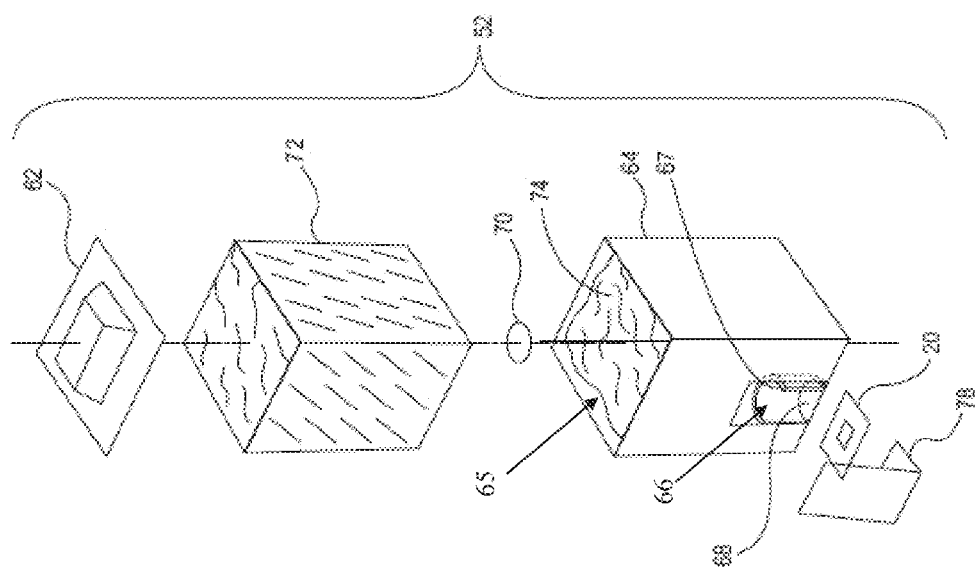
FIG. 2 is an exploded view of a cartridge containing the cosmetic ink composition described herein.

FIG. 2 shows an exploded view of cartridge 52 comprising cartridge cap 62 and cartridge body 64 which defines cartridge reservoir 65. Cartridge body 64 can include standpipe 66 which is typically enclosed within cartridge body 64 and defines nozzle outlet 68. Standpipe 66 can have a standpipe wall 67 that defines a standpipe volume. The ratio of the cartridge reservoir volume to the standpipe reservoir volume can be from about 50:1 to about 3:1, preferably from about 20:1 to about 4:1, and more preferably about 8:1. The standpipe reservoir volume can be from about 0.5 mL to about 3 mL, alternatively from about 0.75 mL to about 2 mL. The standpipe reservoir volume can preferably be about 1 mL. Optional filter 70 can help keep excessively large particles, and other debris out of nozzle array 20. Filter 70 and nozzle array 20 can be on opposite sides of nozzle outlet 68. Cosmetic ink composition 74 can be contained within cartridge body 64. Foam core 72 can at least partially fill cartridge 64 and helps to regulate back pressure of cosmetic ink composition 74. Back pressure can be regulated via bladders (not shown) and other methods known to the art. Foam core 72 shown here is just one example of how to help regulate the flow of the cosmetic ink composition 74 to standpipe 66 through filter 70 and into nozzle array 20. Connector 78 can provide the electrical power and signal to nozzle array 20. Cosmetic ink composition 74 may be ejected from the cartridge 52 by piezoelectric means, thermal means, mechanical pumping means, or a combination of these.

An exemplary cartridge for use herein can include cartridges described in patent application US 2002/0167566.

There is no technical difference between an image used for background L values and those used for local L values, the difference is in the analysis of the image. Hence, the images are continually sent to the processor to calculate the L values and $\Delta L_M$ values. By "sent" it is understood, that preferably at least 4 bits of data per pixel are transferred for each image, and preferably, this 4-bit (or more) packet of data is used in the calculation of each local L value.

It is understood, that the background L can be calculated once in a treatment period and that value can be reused throughout the treatment period. Alternatively, it can be continually recalculated as long as the treatment process goes on. Moreover, there can be pre-programmed triggers to initiate a recalculation of the background L. Also, the background L may be retrieved from the processor memory to be used for the current background L.

When the $\Delta L_M$ exceeds the predetermined value, the cosmetic ink composition can be deposited onto at least a portion of the skin imperfection. In particular, the cosmetic ink composition can be deposited via an array of nozzles and the local L can be calculated along the length of, and in the firing range of, the array of nozzles. An individual nozzle may be fired to deposit the cosmetic ink composition, or multiple nozzles can be fired at the same time. The number of nozzles fired along the array of nozzles can be adjusted based on the size of the $\Delta L_M$ and the size of the skin imperfection. Furthermore, the frequency of nozzle firing can be adjusted based on the $\Delta L_M$, with more droplets being fired in succession in response to larger $\Delta L_M$ values.

The personal care device may deposit the cosmetic ink composition in droplets having an average diameter of from about from about 0.1 μm to about 60 μm, alternatively from about 1 μm to about 50 μm, alternatively from about 5 μm to about 40 μm. Preferably, the cosmetic ink composition can be applied to the skin imperfection in a discontinuous pattern of discrete droplets.

The cosmetic ink composition can be printed from a cartridge having a micro-electro-mechanical system (MEMS) that is different from typical consumer printing applications. It is known that the typical chamber height and nozzle plate thicknesses are from about 25 to about 50 μm since typical printing inks have a viscosity of less than about 10 cP. In one aspect, the cartridge can comprise a chamber height and nozzle plate thicknesses of from about 10 to about 20 μm, preferably from about 12 to about 17 μm. Without being limited by theory it is believed that the shorter chamber height and plate thickness can help minimize viscous loss. In addition, most consumer printing applications are optimized for printing at 10 kHz or more, so ink formulas and microfluidics are designed to achieve rapid refill. However, operating the cosmetic ink composition described herein at this frequency range can result in streaming and/or de-priming due to gulping of air.

The cosmetic ink composition can be printed using the following start-up sequence: heating the substrate to about 60° C. for less than about 600 ms, firing the nozzles in a burst of from about 100 to about 500 fires at a frequency of about 300 to about 1000 Hz, and then maintaining the low shear condition with continuous 4 Hz firing. While it is possible the nozzles will start up with different algorithms, it is likely that the cosmetic ink composition would not be transitioned from its viscous at-rest state to a flowing state.

Also described herein is a method for depositing the cosmetic ink composition onto skin. The method for depositing a cosmetic ink composition onto skin can comprise the steps of:

a. providing a personal care device comprising one or more nozzles and a cartridge operatively associated with the one or more nozzles, wherein a cosmetic ink composition is disposed within the cartridge; and b. depositing the cosmetic ink composition onto a portion of skin, wherein the cosmetic ink composition is deposited in a discontinuous droplet pattern.

More specifically, a method for depositing a cosmetic ink composition onto skin can comprise the steps of:

a. providing a personal care device comprising an array of nozzles;

b. providing a background lightness (L) value;

c. obtaining a treatment image of skin and calculating at least one local L value of individual pixels or group of pixels within the treatment image;

d. comparing the local L value to the background L value;

e. identifying a skin deviation where the absolute value of the difference between the local L value and the background L value is greater than a predetermined set delta L value; and treating the skin deviation with a cosmetic ink composition;

wherein the ink composition comprises a particulate material having a Particle Size Distribution D50 of from about 100 nm to about 2,000 nm; polymeric dispersant having a weight average molecular weight of less than about 20,000 daltons; and a polymeric rheology modifier; wherein the cosmetic ink composition has from about 0.1 to about 20 mm of separation after 11 days of static storage at 40° C., 1 atm, 60% relative humidity, in an 8-dram glass vial, wherein the separation is syneresis.

EXAMPLES AND DATA

The following data and examples, including comparative examples, are provided to help illustrate cosmetic ink compositions described herein. The exemplified compositions are given solely for the purpose of illustration and are not to be construed as limitations of the present invention, as many variations thereof are possible without departing from the spirit and scope of the invention. All parts, percentages, and ratios herein are by weight unless otherwise specified.

Formulas were prepared to assess the impact of the polymeric dispersant and polymeric rheology modifier on the viscosity and separation of the cosmetic ink composition. Examples 1-4 were made according to the procedure described hereafter. Example 1 illustrates a cosmetic ink composition containing the polymeric dispersant sodium polyacrylate (Darvan® 811D) and the HASE type polymeric rheology modifier ACULYN™ Excel (available from The Dow Chemical Company (Lake Zurich, Ill.). Example 2 is a comparative example containing no polymeric rheology modifier. Example 3 is a comparative example containing no polymeric dispersant. Example 4 is a comparative example containing a C12/C14 amine oxide as a molecular rheology modifier.

Examples 1-4 were made according to the following formulas. Weight percent is shown as added.

TABLE 1

| Phase | Description | 1 wt % | 2 wt % | 3 wt % | 4 wt % |
|---|---|---|---|---|---|
| A | 75 wt % TiO$_2$ Slurry (WPG75PFSP)[1] | 12.18 | 11.54 | 12.18 | 15.81 |
| A | 45 wt % Iron Oxide Slurry (WPG45GYSP)[1] | 1.78 | 2.82 | 1.78 | 2.31 |
| A | 55 wt % Iron Oxide Slurry (WPG55GRSP)[1] | 0.11 | 0 | 0.11 | 0 |
| A | 45 wt % Iron Oxide Slurry (WPG45SIRSP)[1] | 0 | 0.14 | 0 | 0.20 |
| B | Deionized Water | 57.53 | 60.30 | 61.73 | 53.98 |
| B | PuraGuard ™ Propylene Glycol[2] | 20.00 | 20.00 | 20.00 | 22.00 |
| B | 50 wt % PVP/VA 735W[3] copolymer in water | 1.00 | 0 | 1.00 | 0 |
| B | Symdiol ® 68[4] | 1.00 | 1.00 | 1.00 | 0 |
| C | 5 wt % Darvan ® 811D[5] in water | 4.20 | 4.20 | 0 | 2.90 |
| D | 15 wt % ACULYN ™ Excel[6] in water | 2.20 | 0 | 2.20 | 0 |
| D | 15% C12/C14 Amine Oxide[7] | 0 | 0 | 0 | 2.80 |

[1] Supplied by KOBO Products Inc (South Plainfield, NJ).
[2] Available from The Dow Chemical Company (Lake Zurich, IL).
[3] Available from Ashland Specialty Chemical (Wilmington, DE).
[4] Hexanediol/Caprylyl Glycol available from Symrise AG (Branchburg, NJ).
[5] Sodium polyacrylate available from Vanderbilt Minerals LLC (Norwalk, CT).
[6] Polyacrylate available from The Dow Chemical Company (Lake Zurich, IL).
[7] Available from The Dow Chemical Company (Lake Zurich, IL).

The samples were stored in sealed glass jars at 50° C. and 60% relative humidity until measurements were performed. The table below shows the PSD, viscosity, tan(delta), and separation for each example. Example 4 was tested at a different time; however, the data are shown together for ease of comparison. PSD is measured according to the Particle Size Distribution Method described hereafter. Viscosity was measured according to the Viscosity Test Method described hereafter. Tan(delta) was calculated by using the storage modulus and loss modulus measured according to the Oscillatory Strain Sweep Method described hereafter. The amount of separation was measured according to the Separation Test Method described hereafter. Separation is recorded in Table 2 as the number of days it took for the sample to reach 2 mm of separation, with the type of separation noted.

TABLE 2

| Ex | Rheology Modifier wt % (active) | Sodium Polyacrylate wt % (active) | PSD D50 (nm) | PSD D90 (nm) | First Dynamic Viscosity 0.1 s$^{-1}$ (cP) | Second Dynamic Viscosity 1000 s$^{-1}$ (cP) | tan delta | Separation at 50° C. Days | Separation at 50° C. Type |
|---|---|---|---|---|---|---|---|---|---|
| 1 | 0.33 | 0.21 | 390 | 660 | 1810 | 35 | 0.62 | 5 | Syneresis |
| 2 | 0 | 0.21 | 390 | 640 | 125 | 2 | 4.11 | <1 | Settling |
| 3 | 0.33 | 0 | 1730 | 3560 | 29400 | 91 | 0.21 | 20 | Syneresis |
| 4 | 0.42 | 0.145 | 4440 | 1200 | 110 | 4 | 5.17 | 2 | Settling |

Example 1 which contained 0.33 active wt % HASE polymeric rheology modifier and 0.21 active wt % polymeric dispersant, had a first dynamic viscosity of 1,810 cP and a second dynamic viscosity of 35 cP, demonstrating that the formula had shear thinning behavior. In addition, Example 1 had agglomeration control as the PSD D90 was maintained under 1 μm. Finally, Example 1 had a tan(delta) below 1 and took 5 days to reach 2 mm of separation with syneresis observed.

Comparative Example 2, which contained 0.21 active wt % polymeric dispersant and no polymeric rheology modifier, had a particle size distribution D90 under 1 μm. However, Comparative Example 2 had a first dynamic viscosity of only 125 cP and was not as shear thinning as compared to Example 1. Comparative Example 2 reached 2 mm of separation in less than 1 day with particle settling observed. It is believed that without the polymeric rheology modifier, the formula could not build enough viscosity to suspend the particles.

It has been previously reported that the HASE polymeric rheology modifier ACULYN™ Excel can provide a thixotropic cosmetic ink composition that is jettable. However, it was found that although Comparative Example 3, which contained 0.33 active wt % ACULYN™ Excel HASE polymeric rheology modifier and no polymeric dispersant, had shear thinning behavior and exhibited syneresis-type separation, it had a PSD D50 4.4 times greater than Example 1, indicating poor particle size control. Comparative Example 3 had a PSD D50 of 1730 nm and a PSD D90 of 3560 nm. It is known that the microfluidic channels in ink cartridges can be very small, for example about from about 10 μm to about 25 μm. As such, it is believed that Comparative Example 3 would likely be difficult to refill in a standard printer ejection head because of the high viscosity and would likely clog the flow channels due to the presence of larger particles. It is also believed that the particles in Comparative Example 3 may not have the optimal size for opacity.

Comparative Example 4 contained 0.42 active wt % C12/C14 amine oxide molecular rheology modifier and 0.145 active wt % polymeric dispersant. It has been previously reported amine oxides may provide some yield stress and may help prevent settling of particles in an ink composition. However, it was surprisingly found that C12/C14 amine oxide in Comparative Example 4 did not build viscosity to the same extent as Example 1 and reached 2 mm of separation with particle settling in only 2 days, demonstrating that the molecular rheology modifier C12/C14 in this formula is not able to build sufficient viscosity to suspend the particles, leading to settling and not syneresis.

In a separate study, different formulas were tested to assess the impact of various types of ASE, HASE, and HEUR polymer rheology modifiers on viscosity and separation of the cosmetic ink composition. Examples 5-17 were prepared according to the procedure described hereinafter.

Examples 5-17 were made according to the formulas in the tables below. Weight percent is shown as added.

TABLE 3

| Phase | Ingredient | 5 wt % | 6 wt % | 7 wt % | 8 wt % | 9 wt % |
|---|---|---|---|---|---|---|
| A | 75 wt % TiO2 Slurry (WPG75PFSP) [1] | 18.46 | 18.46 | 15.00 | 15.00 | 15.00 |
| A | 45 wt % Iron Oxide Slurry (WPG45GYSP) [1] | 4.51 | 4.51 | 3.67 | 3.67 | 3.67 |
| A | 45 wt % Iron Oxide Slurry (WPG45SIRSP) [1] | 0.29 | 0.29 | 0.22 | 0.22 | 0.22 |
| A | Deionized Water | 10.00 | 10.00 | 10.00 | 10.00 | 10.00 |
| B | Deionized Water | 37.8 | 37.14 | 43.51 | 40.51 | 39.90 |
| B | PuraGuard ™ Propylene Glycol[2] | 23.00 | 23.00 | 23.00 | 23.00 | 23.00 |
| C | 5 wt % Darvan ® 811D[5] in water | 2.60 | 2.60 | 2.60 | 4.00 | 4.00 |
| D | 15 wt % ACRYSOL ™ TT615[2] in water | 3.33 | 0 | 0 | 0 | 0 |
| D | 15 wt % Rheovis ® AS1125[12] in water | 0 | 3.33 | 0 | 0 | 0 |
| D | 15 wt % ACULYN ™ Excel[6] in water | 0 | 0 | 2.00 | 0 | 0 |
| D | 15 wt % ACULYN ™ 22[2] in water | 0 | 0 | 0 | 3.60 | 0 |
| D | 15 wt % ACULYN ™ 33[2] in water | 0 | 0 | 0 | 0 | 3.93 |

| Phase | Ingredient | 10 wt % | 11 wt % | 12 wt % | 13 wt % | 14 wt % |
|---|---|---|---|---|---|---|
| A | 75 wt % TiO2 Slurry (WPG75PFSP) [1] | 15.00 | 15.00 | 15.00 | 15.00 | 15.00 |
| A | 45 wt % Iron Oxide Slurry (WPG45GYSP) [1] | 3.67 | 3.67 | 3.66 | 3.66 | 3.66 |
| A | 45 wt % Iron Oxide Slurry (WPG45SIRSP) [1] | 0.22 | 0.22 | 0.22 | 0.22 | 0.22 |
| A | Deionized Water | 10.00 | 10.00 | 10.00 | 10.00 | 10.00 |
| B | Deionized Water | 40.31 | 39.11 | 39.60 | 40.52 | 37.72 |
| B | PuraGuard ™ Propylene Glycol[2] | 23.00 | 23.00 | 23.00 | 23.00 | 23.00 |
| C | 5 wt % Darvan ® 811D[5] in water | 4.00 | 4.00 | 4.00 | 4.00 | 4.00 |
| D | 15 wt % ACULYN ™ 38[2] in water | 3.80 | 0 | 0 | 0 | 0 |
| D | 15 wt % ACULYN ™ 88[2] in water | 0 | 5.00 | 0 | 0 | 0 |
| D | 15 wt % Rheovis ® 1152[12] in water | 0 | 0 | 4.53 | 0 | 0 |
| D | 15 wt % Rheovis ® 1156[12] in water | 0 | 0 | 0 | 3.60 | 0 |
| D | 15 wt % ACRYSOL ™ TT935[2] in water | 0 | 0 | 0 | 0 | 6.40 |

| Phase | Ingredient | 15 wt % | 16 wt % | 17 wt % |
|---|---|---|---|---|
| A | 75 wt % TiO2 Slurry (WPG75PFSP) [1] | 15.00 | 15.00 | 15.00 |
| A | 45 wt % Iron Oxide Slurry (WPG45GYSP) [1] | 3.66 | 3.66 | 3.66 |
| A | 45 wt % Iron Oxide Slurry (WPG45SIRSP) [1] | 0.22 | 0.22 | 0.22 |
| A | Deionized Water | 10.00 | 10.00 | 10.00 |
| B | Deionized Water | 40.26 | 32.18 | 32.18 |
| B | PuraGuard ™ Propylene Glycol[2] | 23.00 | 23.00 | 23.00 |
| C | 5 wt % Darvan ® 811D[5] in water | 4.00 | 2.60 | 2.60 |
| D | 15 wt % ACRYSOL ™ DR300[2] solution | 3.86 | 0 | 0 |
| D | 15 wt % ACULYN ™ 44[2] in water | 0 | 12.40 | 0 |
| D | 15 wt % ACULYN ™ 46N[2] in water | 0 | 0 | 12.47 |

[1] Supplied by KOBO Products Inc (South Plainfield, NJ).
[2] Available from The Dow Chemical Company (Lake Zurich, IL).
[5] Sodium polyacrylate available from Vanderbilt Minerals LLC (Norwalk, CT).
[6] Polyacrylate available from The Dow Chemical Company (Lake Zurich, IL).
[12] Available from BASF (Florham Park, NJ).

The samples were stored in sealed glass jars at 25° C. or 40° C. and 60% relative humidity until measurements were performed. The table below shows the viscosity, tan(delta), and amount and type of separation measured 11 days after formulation for each example. Viscosity was measured according to the Viscosity Test Method described hereafter. Tan(delta) was calculated using the storage modulus and loss modulus measured according to the Oscillatory Strain Sweep Method described hereafter. Separation was measured according to the Separation Test Method described hereafter.

TABLE 4

| Ex | Rheology Modifier Name | Type | wt % (active) | Sodium Polyacrylate wt % (active) | Viscosity 0.1 s$^{-1}$ (cP) | Viscosity 1000 s$^{-1}$ (cP) | tan (delta) | Separation at 11 days 25° C. (mm) | Separation at 11 days 40° C. (mm) | Type |
|---|---|---|---|---|---|---|---|---|---|---|
| 5 | ACRYSOL ™ TT615 | HASE | 0.50 | 0.13 | 6290 | 76 | 0.61 | 1 | 16 | Syneresis |
| 6 | Rheovis ® AS1125 | ASE | 0.50 | 0.13 | 2040 | 73 | 0.68 | 2 | 3 | Syneresis |
| 7 | ACULYN ™ Excel | HASE | 0.30 | 0.13 | 3180 | 37 | 0.54 | 0 | 0 | None |
| 8 | ACULYN ™ 22 | HASE | 0.54 | 0.2 | 4670 | 71 | 0.43 | 0 | 14 | Syneresis |
| 9 | ACULYN ™ 33 | ASE | 0.59 | 0.2 | 4040 | 63 | 0.41 | 0 | 0 | None |
| 10 | ACULYN ™ 38 | ASE | 0.57 | 0.2 | 2280 | 42 | 0.49 | 0 | 1.5 | Syneresis |
| 11 | ACULYN ™ 88 | HASE | 0.75 | 0.2 | 4320 | 71 | 0.50 | 0.5 | 1.5 | Syneresis |
| 12 | Rheovis ® 1152 | HASE | 0.68 | 0.2 | 3060 | 80 | 0.95 | 3.5 | 25 | Syneresis |
| 13 | Rheovis ® 1156 | HASE | 0.54 | 0.2 | 1290 | 69 | 1.77 | 21 | 40 | Syneresis |
| 14 | ACRYSOL ™ TT935 | HASE | 0.96 | 0.2 | 763 | 61 | 1.89 | 37 | 46 | Syneresis |

TABLE 4-continued

| | Rheology Modifier | | Sodium Polyacrylate | Viscosity | | | Separation at 11 days | | |
|---|---|---|---|---|---|---|---|---|---|
| Ex | Name | Type | wt % (active) | wt % (active) | 0.1 s$^{-1}$ (cP) | 1000 s$^{-1}$ (cP) | tan (delta) | 25° C. (mm) | 40° C. (mm) | Type |
| 15 | ACRYSOL ™ DR300 | ASE | 0.58 | 0.2 | 624 | 43 | 1.64 | 43 | 49.5 | Syneresis |
| 16 | ACULYN ™ 44 | HEUR | 1.86 | 0.13 | 194 | 22 | 3.30 | 46 | 49.5 | Settling |
| 17 | ACULYN ™ 46N | HEUR | 1.87 | 0.13 | 460 | 32 | 4.15 | 48 | 52 | Settling |

Without being bound by theory, it is believed that the interaction of the rheology modifier with the particle surface and the polymeric dispersant can form a weak colloidal gel. This weak colloidal gel can introduce elasticity in the composition (as demonstrated by the storage modulus of the cosmetic ink composition) along with viscosity (as demonstrated by the loss modulus of the cosmetic ink composition). Particle suspension can be achieved for cosmetic ink compositions having a low ratio of G" to G', i.e. a tan(delta) of preferably less than about 1, more preferably less than about 0.60.

It was found that Examples 5-12, which all had a first dynamic viscosity of greater than 2,000 cP and a tan(delta) of less than 1, had less than 4 mm of syneresis-type separation at 11 days at 25° C. Under accelerated temperature conditions, Examples 5-12 had 25 mm of syneresis-type separation or less at 11 days. Examples 7 and 9 had no separation (syneresis or settling) at 11 days under both temperature conditions tested.

Although Example 13 had a first dynamic viscosity of 1,290 cP, the tan(delta) was greater than 1 and 21 mm of syneresis-type separation was observed at 11 days. Examples 14 and 15 were not able to build a sufficient viscosity to fully suspend the particles, as demonstrated by the first dynamic viscosity of well below 1,100 cP and the high level of syneresis-type separation at both temperature conditions. Without being limited by theory, it is believed that these formulas were not able to form a colloidal gel capable of keeping the particles in suspension because the formulations comprised too many hydrophobic moieties. Without being bound by theory, it is believed that the degree of syneresis-type separation observed in Example 12 at 50° C. and Examples 13-15 at both temperatures may be too large for these compositions to be jettable and/or may result in inconsistent print quality when jetted.

Examples 16 and 17 which contained HEUR type polymeric rheology modifiers, had a first dynamic viscosity of less than 500 cP and a tan(delta) of well above 1. Examples 16 and 17 were not able to build sufficient viscosity to suspend the particles and had over 45 mm of separation with particle settling at 11 days under both temperature conditions.

In a separate study, different formulas were tested to assess the ability to print the formula from an inkjet cartridge. Examples 18 and 19 were made according to the following formulas. Weight percent is shown as added.

TABLE 5

| Phase | Description | 18 wt % | 19 wt % |
|---|---|---|---|
| A | 75 wt % TiO$_2$ Slurry (WPG75PFSP)[1] | 15.82 | 22.88 |
| A | 45 wt % Iron Oxide Slurry (WPG45GYSP)[1] | 2.31 | 2.60 |
| A | 45 wt % Iron Oxide Slurry WPG45SIRSP)[1] | 0.20 | 0.21 |

TABLE 5-continued

| Phase | Description | 18 wt % | 19 wt % |
|---|---|---|---|
| B | Deionized Water | 48.66 | 45.81 |
| B | PuraGuard ™ Propylene Glycol[2] | 23.00 | 22.50 |
| B | Symdiol ® 68[3] | 0 | 1.00 |
| C | 5 wt % Darvan ® 811D[4] in water (Polymeric Dispersant) | 3.54 | 1.00 |
| D | 15 wt % ACULYN ™ Excel[5] in water (Rheology modifier) | 2.47 | 0 |
| E | 5 wt % Undecylenoyl Phenylalanine[6] | 4.00 | 4.00 |

[1]Supplied by KOBO Products Inc (South Plainfield, NJ).
[2]Available from The Dow Chemical Company (Lake Zurich, IL).
[3]Hexanediol/Caprylyl Glycol available from Symrise AG (Branchburg, NJ).
[4]Available from Ashland Specialty Chemical (Wilmington, DE).
[5]Polyacrylate available from The Dow Chemical Company (Lake Zurich, IL).
[6]Premix made with aminomethyl propanol Ultra PC 2000 available from Angus Chemical (Buffalo Grove, IL), pH > 7. Material available from Seppic (Fairfield, NJ).

The samples were prepared and placed in the inkjet cartridge described above in FIG. 2. To fill the cartridges, the samples were first de-gassed for up to 10 minutes using a vacuum chamber connected to a vacuum pump by conventional methods. The cartridges were then filled using a vacuum fill process. A cartridge holder was equipped with an empty cartridge with a needle and tubing inserted into the cartridge through the cartridge fill hole. The cartridge holder, cartridge, needle, and tubing was placed in the vacuum chamber. The tubing was inserted through the vacuum chamber fill hole that is equipped with a valve to seal the fill hole. A syringe with 4-5 grams of sample was placed at the end of the tubing outside of the vacuum chamber. The vacuum chamber was then closed and the pump was turned on to pull a vacuum to approximately 28 inHg. The pump was turned off and valve opened to allow formula to fill the empty cartridge. After all the contents of the syringe was filled into the cartridge, the vacuum chamber pressure release valve was opened to retrieve the cartridge. After filling, cartridges were placed in the personal care device described herein, and then evaluated for print quality according to the Contrast Ratio Test Method and Nozzle Test Method. The results are shown in Table 6.

TABLE 6

| | Cartridge | |
|---|---|---|
| Composition | C1 Example 18 | C2 Example 19 |
| Printed Contrast Ratio | 20.4% | 23.7% |
| Number of working nozzles (out of 120 total nozzles) | 120 | 120 |

Examples 18 and 19 were both homogeneous prior to printing. Examples 18 and 19 printed from the cartridges and exhibited a printed contrast ratio of 20.4% and 23.7%, respectively, without any nozzle clogging.

Figure 3C:
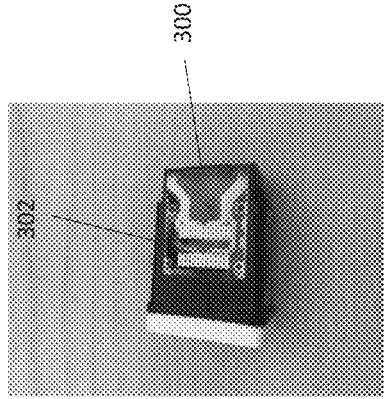
FIG. 3C shows a cartridge with a flex up orientation.
Figure 3B:
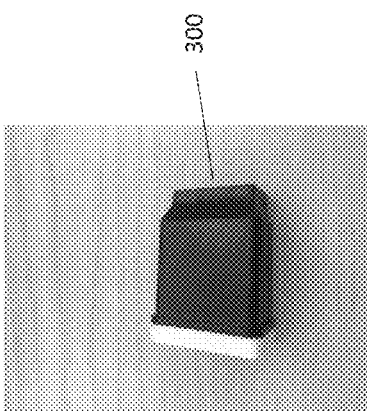
FIG. 3B shows a cartridge with a flex down orientation.
Figure 3A:
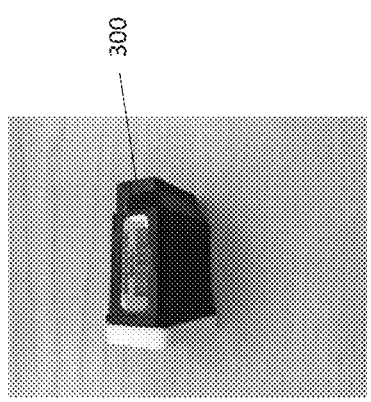
FIG. 3A shows a cartridge with a side orientation.
Figure 3E:
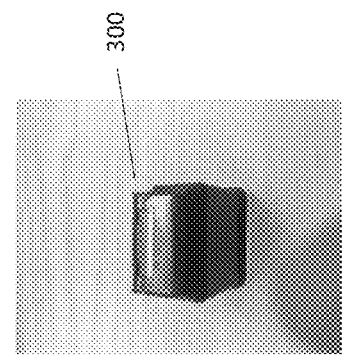
FIG. 3E shows the cartridge with nozzles down orientation.
Figure 3D:
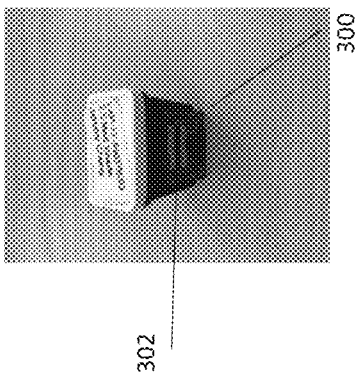
FIG. 3D shows a cartridge with nozzles down orientation.

Next, cartridges containing Example 18 were aged for four weeks at 40° C. and 75% relative humidity (RH) under static conditions under different orientations, with one cartridge in each orientation. FIGS. 3A-3E show the cartridge aging orientations, demonstrating the position of nozzles 300 and flex 302. FIG. 3A shows the cartridge in a side orientation. FIG. 3B shows the cartridge with the flex 302 down. FIG. 3C shows the cartridge with the flex 302 up. FIG. 3D shows the cartridge with nozzles 300 down. FIG. 3E shows the cartridge with the nozzles 300 up. Cartridges containing Example 19 were aged in separate experiments for 7 days at 25° C. and 60% RH (Cartridge $C_8$) and for four weeks at 40° C. and 75% RH (Cartridge C9) under static conditions in the side orientation shown in FIG. 3A. Example 19 was only aged in the side orientation. It is believed that storage in the side orientation is the best for nozzle health. After aging, the cartridges (as indicated in table 7) were tested for separation using the Micro-CT Method described hereinafter. The volume low density represents the particle-lean, low viscosity phase, while the volume high density represents the gel phase.

The aged cartridges (as indicated in table 7) were then subjected to a series of printing cycles to assess the ability to print the test composition. Before printing, the cartridge nozzles were wiped with propylene glycol. The cartridge was then inserted into the personal care device described herein and the composition evaluated for print quality according to the Contrast Ratio Test Method and Nozzle Test Method. A print cycle is defined as printing 360,000 drops distributed over the 120 nozzles in 4 minutes at a print frequency of 3,000 Hz. Printed contrast ratio is recorded as the average value after 40 print cycles.

The results of each study are shown together in table 7 for ease of comparison.

contrast ratio of 40 cycles was 24.2%. Thirty of the nozzles were initially blocked on cartridge C4, but the first print cycle exhibited an acceptable contrast ratio. All nozzles unclogged and were working by the second cycle and the average printed contrast ratio of 40 cycles was 25.2%. Cartridge C5 had three nozzles out during the first cycle and low contrast ratio, however, all nozzles worked on the second cycle. The average contrast ratio of 40 cycles was 27.4%. Ten nozzles were out for cartridge C6, but it exhibited good contrast ratio on the first cycle and all nozzles recovered for the second cycle. The average contrast ratio of 40 cycles was 24.6%. Cartridge C7 had only 81 working nozzles during the first cycle and the contrast ratio was low; however, surprisingly all nozzles recovered during the second cycle. The average contrast ratio of 40 cycles was 28.0%. Cartridge C8 had all 120 nozzles clogged and did not print on the first cycle. Based on the micro-CT data, it is believed that most of Example 19 contained within cartridge C8 separated during aging, and therefore, the particles settled into the nozzles which prevented any printing. It is believed that further aging at 4 weeks, 40° C. worsens this effect and therefore C8 was not able to fire at all.

The ability to print from a cartridge that exhibits syneresis is surprising. Even more surprising, is the ability of cartridges C4-C7 to have some nozzles not work on the first cycle, but fully recover for the second and all subsequent cycles. Without being limited by theory, it is believed that this is enabled by the syneresis and formation of a particle-lean, low viscosity phase. The particle-lean phase expelled by the weak colloidal gel is thought to be rich in humectant and exhibits a low viscosity. These are properties that are desirable for nozzle health and recovery. The particle-lean, low viscosity phase can allow for efficient start-up of the nozzles and recovery of any non-functioning nozzles after a

TABLE 7

| Cartridge | C3 | C4 | C5 | C6 | C7 | C8 | C9 |
|---|---|---|---|---|---|---|---|
| Ink Composition | | Example 18 | | | | Example 19 | |
| Aging Orientation | Side | Flex Down | Flex Up | Nozzles Down | Nozzles Up | Side | Side |
| Aging Conditions | | 4 Weeks, 40° C., 75% RH | | | | 1 Week, 25° C., 60% RH | 4 Weeks, 40° C., 75% RH |
| Volume Low Density (mm³) | 44 | 58 | 68 | 58 | 61 | 456 | Not measured |
| Volume High Density (mm³) | 204 | 72 | 76 | 72 | 89 | 14 | Not measured |
| % separation | 18 | 44 | 47 | 19 | 41 | 97 | Not measured |
| Working Nozzles on 1st cycle | 120 | 90 | 117 | 110 | 81 | Not measured | 0 |
| Working Nozzles on 2nd cycle | 120 | 120 | 120 | 120 | 120 | Not measured | 0 |
| 40 cycle Avg. Printed Contrast Ratio | 24.2% | 25.2% | 27.4% | 24.6% | 28.0% | Not measured | 0 |

It was found that cartridges C3-C7 had between 18% and 47% separation after aging for 4 weeks at 40° C., 75% RH. Conversely, cartridge C8 showed 97% separation after only 7 days at 25° C., 60% RH. Although the aging conditions were different, it was found that most of the separation of occurred within the first 7 days.

All the nozzles of cartridge C3 were working on the first cycle, however, the contrast ratio (opacity) was low on the first cycle of printing. Surprisingly, the second print cycle exhibited an increase in opacity and the average printed single print cycle. The act of printing a cosmetic ink composition with syneresis is sufficient to both recover any non-working nozzles and provide acceptable printed contrast ratio.

Examples 1-4 were made according to the following procedure.

First, the ingredients of Phase A were combined in an appropriate premix container and mixed for 30 minutes. The ingredients of Phase B were added into a main container. Phase B was mixed using a mixer with a propeller blade, such as a digital Eurostar 400® available from IKA® (Staufen im Breisgau, Germany) or equivalent, at low speed until the mixture was homogenous. The pH of the Phase B mixture was measured. Then, the contents of the premix container were transferred into the main container and mixed for 30 minutes. Approximately 10% of the water was withheld from Phase B and was used to wash the premix container and then added to the main container while mixing. Phase C was added to the main container. The mixing speed was increased to high speed and mixing continued for 10 minutes. Phase D was then added dropwise to the main container and the pH was maintained between 7.5-8.5 by adding 20% KOH. Homogeneity was ensured and the mixture was poured into a container, labeled, and stored at ambient conditions before use.

Examples 5-17 were prepared according to the following procedure.

First, the ingredients of Phase A were combined in an appropriate premix container and mixed for 30 minutes. The ingredients of Phase B were added into a main container. Phase B was mixed using a mixer with a propeller blade, such as a digital Eurostar 400® available from IKA® (Staufen im Breisgau, Germany) or equivalent, at low speed until the mixture was homogenous. The pH of the Phase B mixture was measured. Then, the contents of the premix container were transferred into the main container and mixed for 30 minutes. Phase C was added to the main container and mixed. The pH of the main container was measured. Phase D was added to the main container dropwise and the pH was maintained between 7.5-8.5 by adding 20% KOH solution. Homogeneity was ensured and the mixture was poured into a container, labeled, and stored at ambient conditions before use.

Examples 18-19 were prepared according to the following procedure.

First, the ingredients of Phase A were combined in an appropriate premix container and mixed for 30 minutes. The ingredients of Phase B were added into a main container. Phase B was mixed using a mixer with a propeller blade, such as a digital Eurostar 400® available from IKA® (Staufen im Breisgau, Germany) or equivalent, at low speed until the mixture was homogenous. The pH of the Phase B mixture was measured. Then, the contents of the premix container were transferred into the main container and mixed for 30 minutes. Phase C was added to the main container and mixed. The pH of the main container was measured. Phase D was added to the main container dropwise and the pH was maintained between 7.5-8.5 by adding 20% KOH solution. Phase E was then added slowly to the main container and mixed. Homogeneity was ensured and the mixture was poured into a container, labeled, and stored at ambient conditions before use.

Particle Size Distribution Method

The particle size distribution is determined using a laser scattering particle size distribution analyzer. A suitable laser scattering particle size distribution analyzer can include a Horiba LA-950V2 (available from Horiba, Ltd., Kyoto, Japan). In this method, the principles of Mie and Fraunhofer scattering theories are used to calculate the size and distribution of particles suspended in a liquid. Results are normally displayed on a volume basis. The application of this method to pigments has been developed using a flow cell procedure.

Samples are prepared by vortexing for 30 seconds with a Vortex Genie 2 to ensure there is no residue in the bottom of the sample vial. 200 mL of deionized (DI) water is added into the instrument reservoir and analyzed as a blank sample. A disposable micro pipet is used to dispense enough sample into the DI water in the instrument until the Transmittance is reduced from 100 down to 90±2%, approximately 250 µL. Results are reported as D50 or D90.

Viscosity Test Method

Viscosity is measured using a rheometer as a function of shear rate. A suitable rheometer can include an Ares M (available from TA Instruments, New Castle, Del.), or equivalent. First, the samples and standards are equilibrated at room temperature prior to analysis. A 50 mm, 2 degree, cone and plate is zeroed prior to testing. While the sample is at 25° C.±0.5° C., the sample is tested. A shear sweep measurement is performed over a range of 0.1-1000 $s^{-1}$ to determine the shear thinning properties and viscosity at different shear rates.

Separation Test Method

Separation is measured by filing an 8-dram (1 oz., 25 mm×95 mm) screw cap glass vial to a height of 55 mm with the sample composition (as measured from the bottom of the vial to the top of the liquid composition). The vials are sealed and are placed in controlled temperature chambers. The vials are held static storage until measurements are performed. At each time point, the vial is carefully removed from the chamber without vigorous or prolonged agitation and observed for any visual signs of separation and the type of separation is noted as syneresis or settling. The amount of separation is determined by measuring the mm of clear fluid at the top of the sample with a digital caliper.

Particle Settling Test Method

Particle settling is measured as follows. An aluminum dish is weighed to determine the dish weight. A 1 gram aliquot of the sample from the top, middle, or bottom of the sample vial is added to the dish and weighed to determine the wet weight. "Top" means the surface of the sample in the vial. "Middle" means the middle of the vial. "Bottom" means the bottom of the vial. The dish with the sample aliquot is placed in an oven at 100° C. for one hour to evaporate the volatiles. The dish is removed and weighed again to get a dry weight. The weight % solids is calculated by the following equation: (dry weight−dish weight)/(wet weight−dish weight).

Micro-CT Separation Method

The micro-CT Separation Method measures the degree of phase separation of cosmetic ink composition sample in the standpipe of an inkjet cartridge based on the density profile differences between phases. This method is based on analysis of a 3D x-ray attenuation profile of the sample obtained on a micro-CT instrument (a suitable instrument is the Scanco µCT 50 available from Scanco Medical AG, Switzerland, or equivalent). The micro-CT instrument is a cone beam microtomograph with a shielded cabinet. A maintenance free x-ray tube is used as the source with an adjustable diameter focal spot. The x-ray beam passes through the sample, where some of the x-rays are attenuated by the sample. The extent of attenuation correlates to the mass and amount of material the x-rays have to pass through. The transmitted x-rays continue on to the digital detector array and generate a 2D projection image of the sample. A 3D image of the sample is generated by collecting several individual projection images of the sample as it is rotated 360-degrees, which are then reconstructed into a single 3D image. The instrument is interfaced with a computer running software to control the image acquisition and reconstruction of the raw data into a 3D image. The 3D image is then analyzed using image analysis software (suitable image analysis software are MATLAB available from The Mathworks, Inc., Natick, Mass., and Avizo Lite available from Visualization Sciences Group/FEI Company, Burlington, Mass., or equivalents) to measure the volume of the particle lean phase relative to the total volume of the 3D image.

Sample Preparation:

Prior to analysis, the composition within the cartridge is homogenized and then the cartridge is placed in static storage at 40° C., 1 atm, and 75% relative humidity for a period of 28 days on a surface normal to the gravitational field with the printing nozzles oriented downward and the standpipe walls normal to the storage surface (FIG. 3D). A brace or bracket may be used to stabilize the cartridge in this orientation if required. Homogenization is achieved by any means of standard practice such as shaking, flipping or agitating the cartridge. Homogenization is confirmed by measuring a micro-CT separation value of less than 5% according to the method described below.

Image Acquisition:

The micro-CT instrument is set up and calibrated according to the manufacturer's specifications. A cartridge is then positioned in the same orientation as storage, with the printing nozzles oriented downward, and mounted on a low density material for stabilization inside a plastic cylindrical tube large enough to fully encompass the cartridge volume. Cartridges are to be transferred with care so as to not induce agitation that would disturb the composition.

A scan of the entire cartridge standpipe is acquired. A single 3D dataset of contiguous 15 μm (microns) isotropic voxels is collected with the XY-dimension in the horizontal plane and the Z-dimension in the vertical. Images are acquired with the source at 70 kVp and 200 μA with an additional 0.5 mm aluminum filter. These current and voltage settings are optimized to produce the maximum contrast in the projection data with sufficient x-ray penetration through the sample with high signal to noise ratio (SNR), but once optimized held constant for all substantially similar samples. A total of 1500 projection images are obtained with an integration time of 600 ms and 4 averages per angle of rotation. The projection images are reconstructed into a 3D dataset having an isotropic spatial resolution of 15 μm (microns), and saved in 16-bit RAW format to preserve the full detector output signal for analysis.

Image Processing:

The 3D dataset is loaded into the image analysis software and scaled from 16-bit to 8-bit. The 3D dataset is trimmed (cropped) to a rectangular prism 3D image by removing the extraneous data surrounding the ink analysis region from the 3D dataset. Trimming is performed such that the maximum volume of the ink within the standpipe is retained in the analysis region, and any portion of the cartridge is excluded. The 3D image is trimmed such the Z-dimension spans the entire height of the ink within the standpipe. The trimmed 3D image is thresholded at a value which separates, and removes, any background signal due to air within the ink analysis region, but maintains the signal from the composition. A second segmentation step is performed using Otsu's method, which calculates the threshold level that minimizes the weighted intra-class variance within the 3D image, to separate the volume of the denser higher attenuating particle rich region from the lower attenuating particle lean region.

The volume of the particle lean region is measured and the Micro-CT Separation Value is calculated as the percent of the lower attenuating particle lean phase volume to the total ink volume in the analysis region, reported to the nearest 1%. A total of three substantially similar replicate inkjet cartridge samples are prepared and analyzed in like manner, and the statistical mean of the three recorded Micro-CT Separation Values is reported to the nearest 1%."

Contrast Ratio Test Method

Contrast ratio can be determined after a sample is printed onto a transparency (Apollo VCG7031SE, or equivalent) on the textured side using a block pattern (120 nozzles, at a frequency of 340+/−10 Hz, 1,000 drops per nozzles, and a speed of 20+/−5 mm/s). The block pattern is placed over an opacity chart (Form N2A, Leneta Company of Manwah, NJ, or the equivalent). The sample is allowed to dry for 1 hour under conditions of 22° C.+/−1° C., 1 atm. Using a spectrophotometer with settings selected to exclude specular reflection, the Y tristimulus value (i.e., the XYZ color space) of the sample is measured and recorded. The Y tristimulus value is measured in three different areas of the sample over the black section of the opacity chart, and also in three different areas of the sample over the white section of the opacity chart.

The contrast ratio is calculated as the mathematical average of the three Y tristimulus values over the black areas, divided by the mathematical average of the three Y tristimulus values over the white areas, times 100:

$$\text{Contrast Ratio} = \frac{\text{average}(Yblack)}{\text{average}(Ywhite)} \times 100$$

Nozzle Test Method

Functioning nozzles are determined as follows. A sample is placed in an inkjet cartridge (a suitable cartridge is described above, or equivalent). The cartridge is placed in an inkjet printer (a suitable inkjet printer is the personal care device described above, or equivalent) and a stair step pattern is printed onto a transparency (Apollo VCG7031SE, or equivalent) on the textured side starting from nozzle 1 to 120, with 50 drops per nozzles, at a frequency of 1,000 Hz and a speed of about 20 mm/s. Functioning nozzles are then counted and reported.

Oscillatory Strain Sweep Method

Oscillatory strain sweep is measured using a rheometer (such as an ARES-G2 available from TA Instruments, New Castle, Del.), or equivalent.

The samples and standards are allowed to equilibrate at ambient conditions prior to analysis. The rheometer is calibrated as disclosed in the operator's manual. The oscillatory strain sweep measurement is performed at a fixed angular frequency of 6.28 rad/s over a strain range of 0.0001-1 using a 40 mm 316SST (APS heat break) parallel plate at 25° C., with a 0.05 mm gap, to determine the storage and loss moduli.

Zeta Potential Test Method

Zeta potential is measured using a Zeta potential analyzer such as a NanoBrook ZetaPALS Potential Analyzer available from Brookhaven Instruments Corporation, Holtsville, N.Y., or equivalent.

Zeta potential test samples are prepared by diluting the sample to 0.1 g/ml into deionized water. Zeta potential is measured on a Zeta potential analyzer using the Smoluchowski Zeta potential model with 5 runs and 10 cycles. After running a standard (BIZR3), the cells of the Zeta potential analyzer are loaded with 1 ml of test sample. Zeta potential is measured as a function of pH.

Combinations

A. A cosmetic ink composition comprising: from 1 to 30 active wt % titanium dioxide having a Particle Size Distribution D50 of 100 nm to 2,000 nm; a polymeric dispersant having a weight average molecular weight of less than 20,000 daltons; and a polymeric rheology modifier; wherein the cosmetic ink composition has from 0.1 to 20 mm of separation after 11 days of static storage at 25° C., 1 atm, 60% relative humidity, in an 8-dram glass vial; wherein the separation is syneresis.

A. The cosmetic ink composition of paragraph A wherein the cosmetic ink composition comprises from 5 to 20 active wt % titanium dioxide, preferably from 10 to 18 active wt %.

B. The cosmetic ink composition of any of the preceding paragraphs wherein the titanium dioxide has a Particle Size Distribution D50 of from 150 nm to 1,000 nm, preferably from 250 nm to 650 nm, and more preferably from 200 nm to 350 nm.

C. The cosmetic ink composition of any of the preceding paragraphs the wherein particulate material has a Particle Size Distribution D90 of from 700 nm to 1250 nm, preferably from 800 nm to 900 nm.

D. The cosmetic ink composition of any of the preceding paragraphs wherein the cosmetic ink composition comprises greater than 0.30 active wt % polymeric rheology modifier.

E. The cosmetic ink composition of any of the preceding paragraphs wherein the polymeric dispersant is a (meth)acrylic acid homopolymer or salt thereof.

F. The cosmetic ink composition of any of the preceding paragraphs wherein the cosmetic ink composition further comprises from 10 to 30 active wt % humectant, preferably from 20 to 30 active wt %.

G. The cosmetic ink composition of any of the preceding paragraphs wherein the cosmetic ink composition has a neat pH of from 7.5 to 9.0.

H. The cosmetic ink composition of any of the preceding paragraphs wherein the polymeric rheology modifier is selected from the group consisting of alkali swellable emulsion polymers, hydrophobically modified alkali swellable emulsion polymers, and combinations thereof.

I. The cosmetic ink composition of paragraph H wherein the polymeric rheology modifier is an alkali swellable acrylic polymer emulsion.

J. The cosmetic ink composition of any of the preceding paragraphs further comprising iron oxide.

K. The cosmetic ink composition of any of the preceding paragraphs wherein the polymeric dispersant has a weight average molecular weight of from 1,000 to 10,000 daltons, preferably from 2,000 to 5,000 daltons.

L. The cosmetic ink composition of any of the preceding paragraphs comprising from 0.01 to 1 active wt % of the polymeric dispersant.

M. The cosmetic ink composition of any of the preceding paragraphs wherein the (meth)acrylic acid homopolymer or salt thereof is sodium polyacrylate.

N. The cosmetic ink composition of any of the preceding paragraphs wherein the cosmetic ink composition has from 0.5 to 15 mm after 11 days of static storage at 25° C. after 11 days of static storage at 40° C., 1 atm, 60% relative humidity, in an 8-dram glass vial.

O. The cosmetic ink composition of any of the preceding paragraphs wherein the cosmetic ink composition has a first dynamic viscosity of 1,100 cP to 10,000 cP at a shear rate of 0.1 sec$^{-1}$ measured at 25° C., preferably 1,500 cP to 8,000 cP, more preferably from 2,000 cP to 5,000 cP, and a second dynamic viscosity of from 10 to 100 cP at a shear rate of 1,000 sec$^{-1}$ measured at 25° C., preferably from 20 to 80 cP.

Values disclosed herein as ends of ranges are not to be understood as being strictly limited to the exact numerical values recited. Instead, unless otherwise specified, each numerical range is intended to mean both the recited values and any integers within the range. For example, a range disclosed as "1 to 10" is intended to mean "1, 2, 3, 4, 5, 6, 7, 8, 9, and 10."

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An ink cartridge containing a cosmetic ink composition comprising:
   a. from about 1 to about 30 active wt % titanium dioxide;
   b. a polymeric dispersant having a weight average molecular weight of less than about 20,000 daltons; and
   c. greater than about 0.3 active wt % of a polymeric rheology modifier selected from the group consisting of alkali swellable emulsion polymers, hydrophobically modified alkali swellable emulsion polymers, and combinations thereof;
   wherein the cosmetic ink composition has a Micro-CT Separation Value of from about 5% to about 50% after 28 days of static storage at 40° C., 1 atm, 75% relative humidity; and
   wherein the cosmetic ink composition has a first dynamic viscosity of from about 1,100 cP to about 10,000 cP at a shear rate of 0.1 sec$^{-1}$ measured at 25° C. and a second dynamic viscosity of less than about 100 cP at a shear rate of 1,000 sec$^{-1}$ measured at 25° C.; wherein the cosmetic ink composition has a tan(delta) of less than about 1.

2. The inkjet cartridge of claim 1 wherein the titanium dioxide has a Particle Size Distribution D90 of from about 800 nm to about 1250 nm.

3. The cosmetic ink composition of claim 1 wherein the polymeric dispersant has a weight average molecular weight of from about 2,000 to about 5,000 daltons.

4. The cosmetic ink composition of claim 1 comprising from about 10 to about 18 active wt % titanium dioxide.

5. The cosmetic ink composition of claim 1 wherein the polymeric dispersant has a weight average molecular weight of from about 1,000 to about 10,000 daltons.

6. The cosmetic ink composition of claim 1 wherein the titanium dioxide has a Particle Size Distribution D50 of from about 250 nm to about 650 nm.

7. The cosmetic ink composition of claim 1 comprising from about 0.01 to about 1 active wt % of the polymeric dispersant.

8. The cosmetic ink composition of claim 1 further comprising from about 10 to about 30 active wt % humectant.

9. The cosmetic ink composition of claim 1 further comprising iron oxide.

10. The cosmetic ink composition of claim 1 wherein the cosmetic ink composition has from about 0.1 to about 20 mm of separation after 11 days of static storage at 40° C., 1 atm, 60% relative humidity, in an 8-dram glass vial; wherein the separation is syneresis.

11. The cosmetic ink composition of claim 1 wherein the polymeric dispersant is a (meth)acrylic acid homopolymer or salt thereof.

* * * * *